(12) United States Patent
Chen et al.

(10) Patent No.: US 10,646,591 B2
(45) Date of Patent: May 12, 2020

(54) IMAGING AGENTS FOR IMAGING PROTEASE ACTIVITY AND USES THEREOF

(71) Applicant: The United States of America, as represented by the Secretary, Department of Health and Human Services, Bethesda, MD (US)

(72) Inventors: Xiaoyuan Chen, Potomac, MD (US); Seulki Lee, Baltimore, MD (US); Lei Zhu, Xiamen (CN)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 13 days.

(21) Appl. No.: 15/337,461

(22) Filed: Oct. 28, 2016

(65) Prior Publication Data

US 2017/0143851 A1 May 25, 2017

Related U.S. Application Data

(62) Division of application No. 14/343,469, filed as application No. PCT/US2012/054121 on Sep. 7, 2012, now abandoned.

(60) Provisional application No. 61/533,014, filed on Sep. 9, 2011.

(51) Int. Cl.
*A61K 49/00* (2006.01)
*A61K 47/65* (2017.01)
*A61N 5/06* (2006.01)

(52) U.S. Cl.
CPC .......... *A61K 49/0032* (2013.01); *A61K 47/65* (2017.08); *A61K 49/0054* (2013.01); *A61K 49/0056* (2013.01); *A61N 5/062* (2013.01)

(58) Field of Classification Search
CPC ............... A61K 49/00; A61K 49/0032; A61K 49/0054; A61K 49/0056; A61K 47/00; A61K 47/65; A61N 5/062
USPC .... 424/1.11, 1.65, 1.81, 1.85, 1.89, 9.1, 9.2, 424/9.6; 530/300
See application file for complete search history.

(56) References Cited

U.S. PATENT DOCUMENTS

| 8,815,214 B2 | 8/2014 | Rajopadhye et al. |
| 2005/0014160 A1 | 1/2005 | Kumaraswamy et al. |
| 2005/0214221 A1 | 9/2005 | Poss et al. |
| 2009/0061532 A1 | 3/2009 | Papineni et al. |
| 2009/0220430 A1* | 9/2009 | Rajopadhye ....... A61K 49/0032 424/9.6 |
| 2011/0213121 A1* | 9/2011 | Kwon ....................... C12Q 1/37 530/322 |

FOREIGN PATENT DOCUMENTS

| WO | WO 2009/092062 A2 | 7/2009 |
| WO | WO 2010/002976 A2 | 1/2010 |

OTHER PUBLICATIONS

European Patent Office, International Preliminary Report on Patentability in International Patent Application No. PCT/US2012/054121, 7 pages (dated Mar. 12, 2014).

(Continued)

*Primary Examiner* — D. L. Jones
(74) *Attorney, Agent, or Firm* — Leydig, Voit & Mayer, Ltd.

(57) ABSTRACT

Disclosed are imaging agents having the following Formula I:

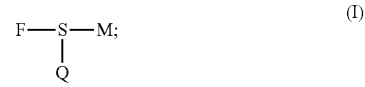

wherein F is a near infrared fluorophore, S is an enzymatically cleavable oligopeptide, Q is a fluorescence quencher molecule, and M is a moiety selected from the group consisting of PEG or derivative thereof and a targeting ligand, and wherein F, Q and M are linked to separate amino acids of the enzymatically cleavable oligopeptide. Compositions comprising such compounds, as well as methods of use, methods of identifying a cell or a population of cells in vivo expressing a protease of interest, and methods of treating a disease through imaging are also disclosed.

12 Claims, 29 Drawing Sheets
Specification includes a Sequence Listing.

(56) References Cited

OTHER PUBLICATIONS

European Patent Office, International Search Report in International Patent Application No. PCT/US2012/054121, 5 pages (dated Dec. 5, 2012).

European Patent Office, Written Opinion of the International Searching Authority in International Patent Application No. PCT/US2012/054121, 6 pages (dated Dec. 5, 2012).

Lee et al., "Activatable Imaging Probes with Amplified Fluorescent Signals," *Chem. Commun.*: 4250-4260 (2008).

Lee et al., "Activatable Molecular Probes for Cancer Imaging," *Current Topics in Medicinal Chemistry*, 10: 1135-1144 (2010).

Lee et al., "Peptides and Peptide Hormones for Molecular Imaging and Disease Diagnosis," *Chem. Rev.*, 110: 3087-3111 (2010).

Lee et al., "Polymeric Nanoparticle-Based Activatable Near-Infrared Nanosensor for Protease Determination In Vivo," *Nano Letters*, 9(12): 4412-4416 (2009).

Ryu et al., " 'One Step' Detection of Matrix Metalloproteinase Activity Using a Flurogenic Peptide Probe-Immobilized Diagnostic Kit," *Bioconjugate Chemistry*, 21: 1378-1384 (2010).

Zhu et al., "Dual-Functional, Receptor-Targeted Fluorogenic Probe for In Vivo Imaging of Extracellular Protease Expressions," *Bioconjugate Chemistry*, 22: 1001-1005 (2011).

Zhu et al., "High-Affinity Peptide Against MT1-MMP for In Vivo Tumor Imaging," *Journal of Controlled Release*, 150: 248-255 (2011).

Zhu et al., "Real-Time Video Imaging of Protease Expression in Vivo," *Theranostics*, 1: 16-25 (2011).

\* cited by examiner

Texas Red

IRDye 650

IRDye 750

IRDye 800

DABCYL

DABSYL

Blackberry Quencher 650

QSY® 7

QSY®9

QSY®21

BHQ1, R =COOH or NH2

BHQ2, R =COOH or NH2

BHQ3, R =COOH or NH2

Eclipse quencher phosphoramidite

Eclipse quencher CPG

SEQUENCE LISTING

```
<160> NUMBER OF SEQ ID NOS: 10

<210> SEQ ID NO 1
<211> LENGTH: 3
<212> TYPE: PRT
<213> ORGANISM: Artificial Sequence
<220> FEATURE:
<223> OTHER INFORMATION: Synthetic

<400> SEQUENCE: 1

Arg Gly Asp
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Arg Gly Asp Tyr Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3
```

```
Gly Pro Leu Gly Val Arg Gly Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Val Pro Leu Ser Leu Thr Met
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Pro Tyr Ala Leu Trp Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Pro Leu Ala Tyr Trp Ala Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Leu Pro Lys Gly Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Arg Pro Lys Pro Val Glu
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic

<400> SEQUENCE: 9
```

```
Val Pro Arg
1

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Gly Pro Leu Gly Val Arg Gly Lys Gly Gly
1               5                   10
```

IMAGING AGENTS FOR IMAGING PROTEASE ACTIVITY AND USES THEREOF

CROSS-REFERENCE TO A RELATED APPLICATION

This patent application is a divisional of U.S. patent application Ser. No. 14/343,469, filed Mar. 7, 2014, which is the U.S. national stage of International Patent Application No. PCT/US2012/054121, filed Sep. 7, 2012, which claims the benefit of U.S. Provisional Patent Application No. 61/533,014, filed Sep. 9, 2011, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,011 Byte ASCII (Text) file named "726973_ST25.TXT," created on Oct. 27, 2016.

BACKGROUND OF THE INVENTION

Most new drug candidates generated during in vitro screening turn out to be invalid after time-consuming and costly testing in animal models. Therefore, there is an urgent need for development of noninvasive, real-time, sensitive, and cost-effective tools with high throughput, for monitoring and early detection of drug efficacy in vivo.

Optical molecular imaging provides many advantages over other imaging modalities, including high sensitivity and safe detection with non-radioactive materials, using readily available instruments, at moderate cost. Peptide-based molecular beacons, otherwise known as protease activatable optical probes or imaging agents, have enabled in vivo imaging of protease activity and demonstrated promising results in the field of protease research and protease-targeted drug development.

Proteases are known as exceptionally critical signaling proteins that are involved in numerous processes, such as inflammation, as well as cancer, neurological disorders, and cardiovascular diseases. Considerable efforts have been made to identify the role of certain proteases in biological processes and to screen specific molecules that can regulate protease expression. There are known experimental methods based on the use of protease reporters or molecular beacons. However, they are limited to in vitro applications.

With the development of hydrophilic near-infrared (NIR) dyes and quenchers, it is now possible to use conventional molecular beacon constructs as in vivo imaging agents. These imaging agents are optically silent (quenched) in their native state and are activated in the presence of a specific protease, thereby generating an NIR fluorescence signal. However, the inherent instability, short half-life, long activation time in vivo and/or nonspecific activation of peptides and small compounds are still major obstacles to their in vivo application via systemic administration.

In view of the foregoing, there currently exists an unmet need for a fast acting and/or extended-use activatable imaging agent which can permit real-time video imaging of protease expression in vivo.

BRIEF SUMMARY OF THE INVENTION

In an embodiment, the present invention provides one or more imaging agents having the following Formula I:

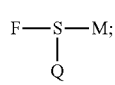

wherein:
F is a near infrared fluorophore;
S is an enzymatically cleavable oligopeptide;
Q is a fluorescence quencher molecule; and
M is a moiety selected from the group consisting of PEG or a derivative thereof and a targeting ligand, wherein PEG is a polyethylene glycol polymer molecule or a derivative thereof, and wherein F, Q and M are linked to separate amino acids of the enzymatically cleavable oligopeptide.

In another embodiment, the present invention provides a composition comprising at least one or more imaging agents of formula I, as set forth above, and a carrier.

In yet another embodiment, the present invention provides one or more imaging agents of formula I, as set forth above, which exhibits maximum fluorescence in less than 24 hours.

In a further embodiment, the present invention provides a method of identifying a cell or a population of cells in vivo expressing a protease of interest comprising a) contacting the cell or a population of cells expressing a protease of interest with at least one or more imaging agents of formula I, as set forth above, which is selectively cleavable by a protease of interest, b) allowing the imaging agent to be selectively cleaved by the protease of interest in the cell or population of cells, and c) detecting the fluorescence of the fluorophore in the imaging agent after being cleaved by the protease of interest in the cell or population of cells.

In another embodiment, the present invention provides a method of diagnosing a disease overexpressing a protease in a subject comprising a) administering to a subject suspected of having said disease, one or more imaging agents of formula I, as set forth above, which is selectively cleavable by a protease of interest, the cleavage of which indicates the presence of the disease, wherein said imaging agent is at least one of the above identified imaging agents, b) allowing the imaging agent to be cleaved by the protease of interest, c) detecting the presence of the fluorophore in the imaging agent binding the protease of interest in the patient, and d) determining whether the subject has a disease overexpressing a protease.

The advantages of the imaging agents of the present invention include images having significantly enhanced target-to-background ratio in tumors overexpressing the target protease utilizing a small molecular weight PEG or derivative as a conjugate, to a fluorescently quenched substrate, and are fast acting.

BRIEF DESCRIPTION OF THE SEVERAL VIEWS OF THE DRAWING(S)

FIG. 1A is a schematic showing the general synthesis of an embodiment of the imaging agents of the present invention which are matrix metalloproteinase (MMP) specific (MMP-$P_n$s) wherein n=4, 12, 24, or 67 as represented by 4. The reagents for each step are as follows: a) HSPyU, 2% DIPEA/DMF, $NH_2$—$R_1$; b) 20% piperidine/DMF; c) Cy5.5-NHS ester, 2% DIPEA/DMF; d) TFA/water/TIS (95/2.5/2.5, v/v/v); e) BHQ-3 NHS ester, 2% DIPEA/DMF FIG. 1B depicts the polyethylene glycol moieties of the different MMP-$P_n$s and the structure of the fluorophore Cy5.5 and quencher BHQ-3.

FIG. 2A is a graph depicting the recovery of fluorescence of the agent MMP-P0 (15 nM) in the presence of various activated MMPs (40 nmol/L) following 80 minute incubation at 37° C.

FIG. 2B is a graph depicting fluorescence activation of the various MMPs (20 nM) in a solution containing activated MMP-13 (40 nmol/L) following 80 minute incubation at 37° C. In this graph, fluorescence emission spectra of the MMPs before (quenched state, low fluorescence intensity, signals enlarged in inset) and after (activated state, increased fluorescence intensity) addition of activated MMP-13.

Figure 3:
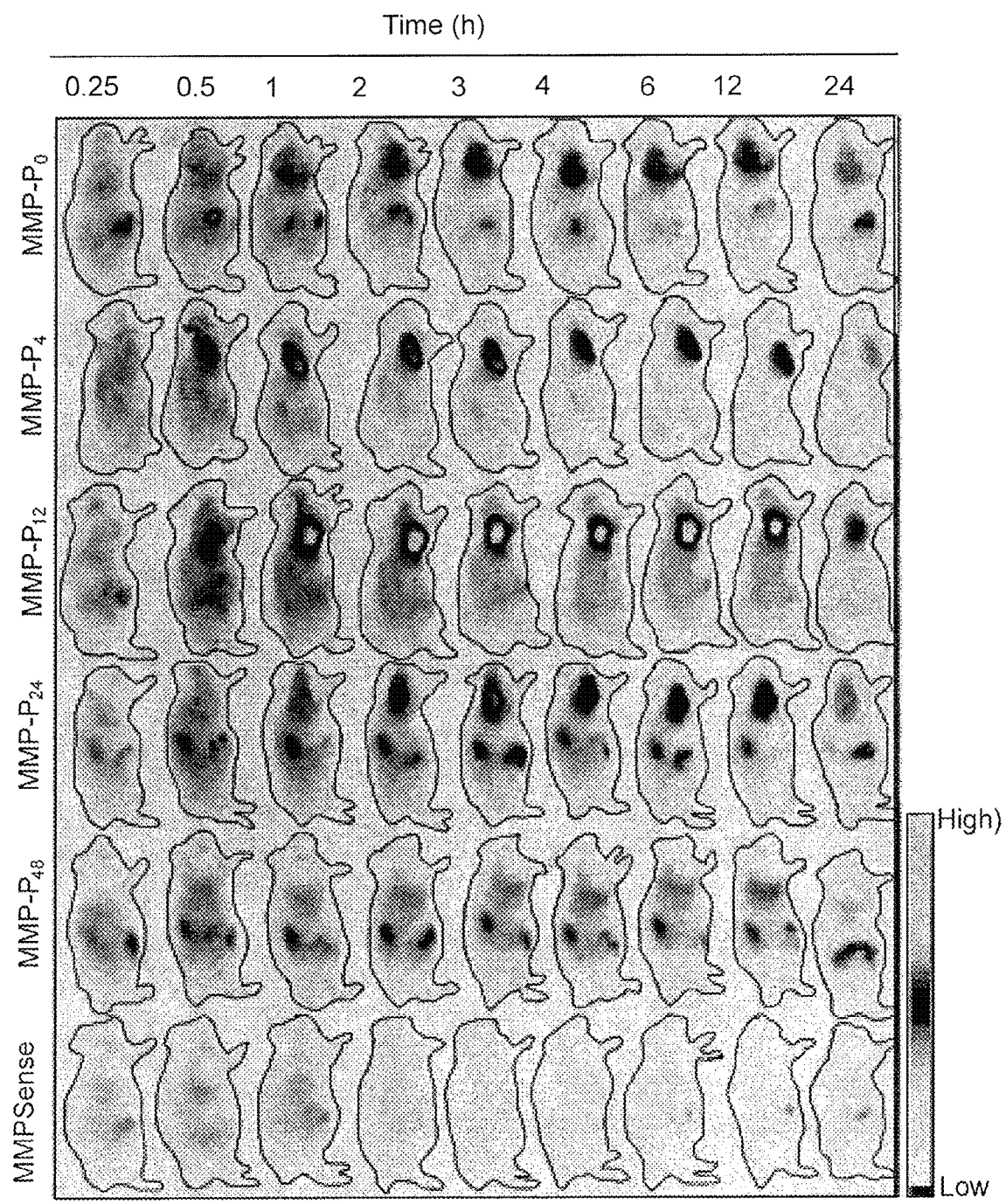

FIG. 3 is an image of whole-mouse imaging with the Maestro 2 imaging system. Representative serial fluorescence images of MMPs-positive SCC7 tumor-bearing mice injected intravenously with the MMP-Ps and MMPSense 680™ are shown. Images were acquired at the indicated time points and were normalized by the maximum average value. The bar indicates radiant efficiency (low, 0; high, 2.62×10$^5$).

Figure 4A:
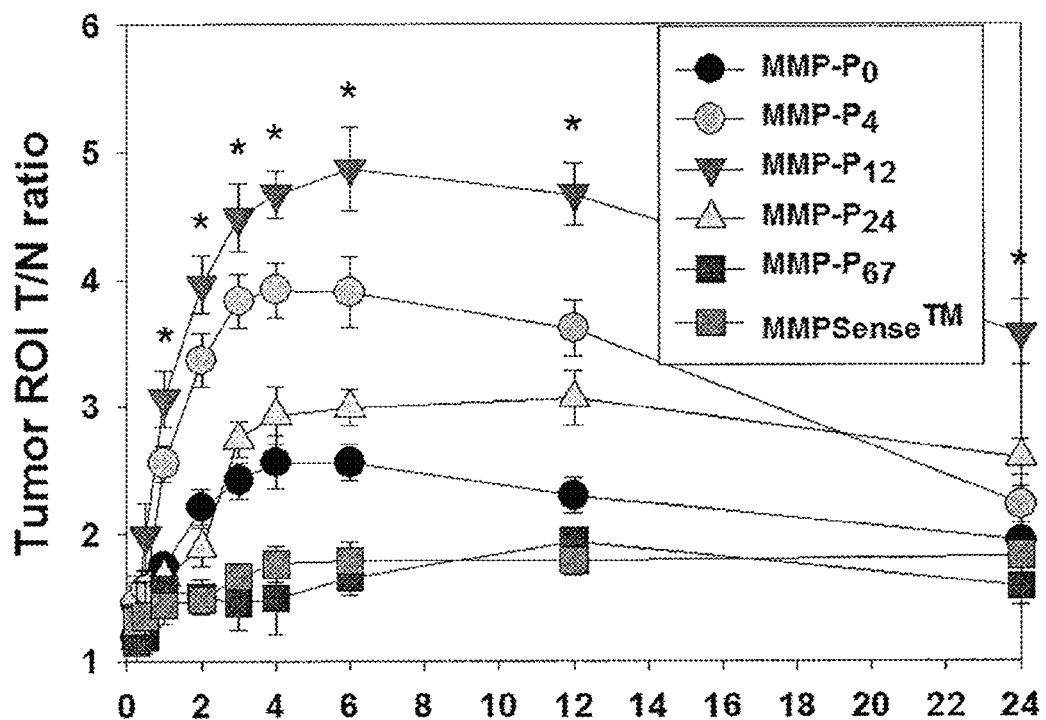

FIG. 4A is a graph depicting the region of interest (ROI) tumor-to-normal tissue (T/N) ratio analysis of fluorescence intensity of SCC7 tumor in vivo.

Figure 4B:
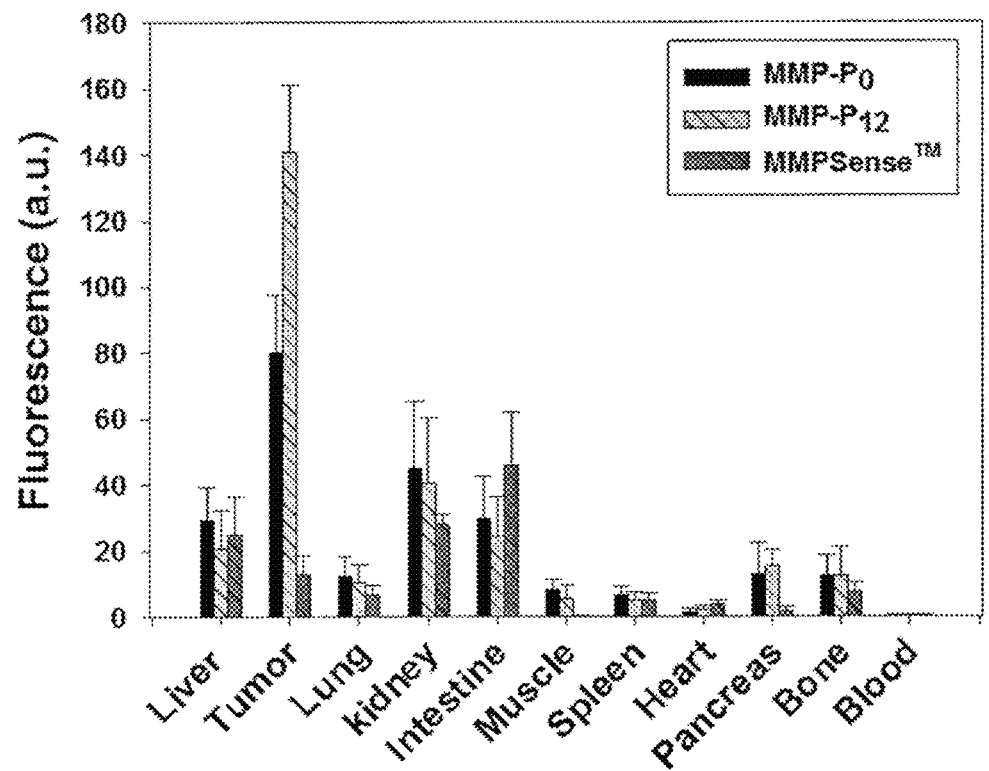

FIG. 4B is a bar graph depicting the biodistribution of the imaging agents MMP-P$_0$, MMP-P$_{12}$ and MMPSense 680™ at 4 hours post-injection. Data are expressed as means±s.d. (n=3-6/group). *P<0.05 (Student's t-test) for agent MMP-P12 relative to other probes.

Figure 5A:
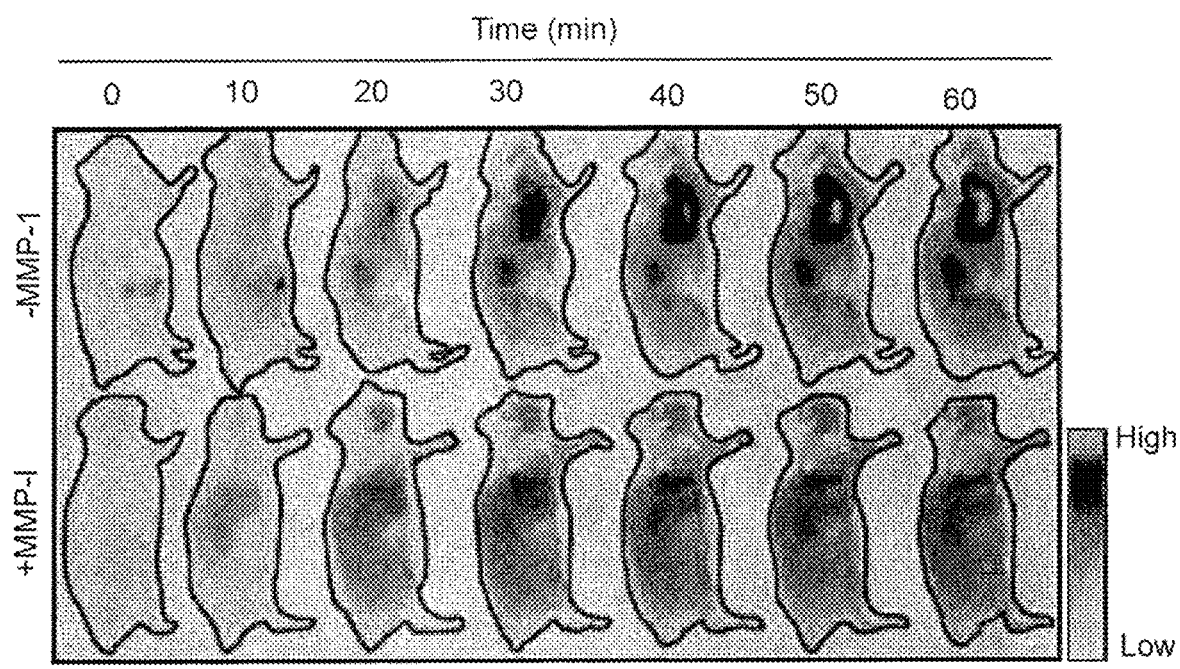

FIG. 5A is a depiction of real-time video imaging of MMP expression in SCC7 tumor-bearing mice. The imaging agent MMP-P12 was injected into mice with or without MMP-I treatment, via tail vein catheter during the imaging procedures. Whole-mouse images were obtained every 10 to 20 seconds for 1 hour. Images were normalized by the maximum average value. The bar indicates radiant efficiency (low, 0; high, 4.8×10$^4$).

Figure 5B:
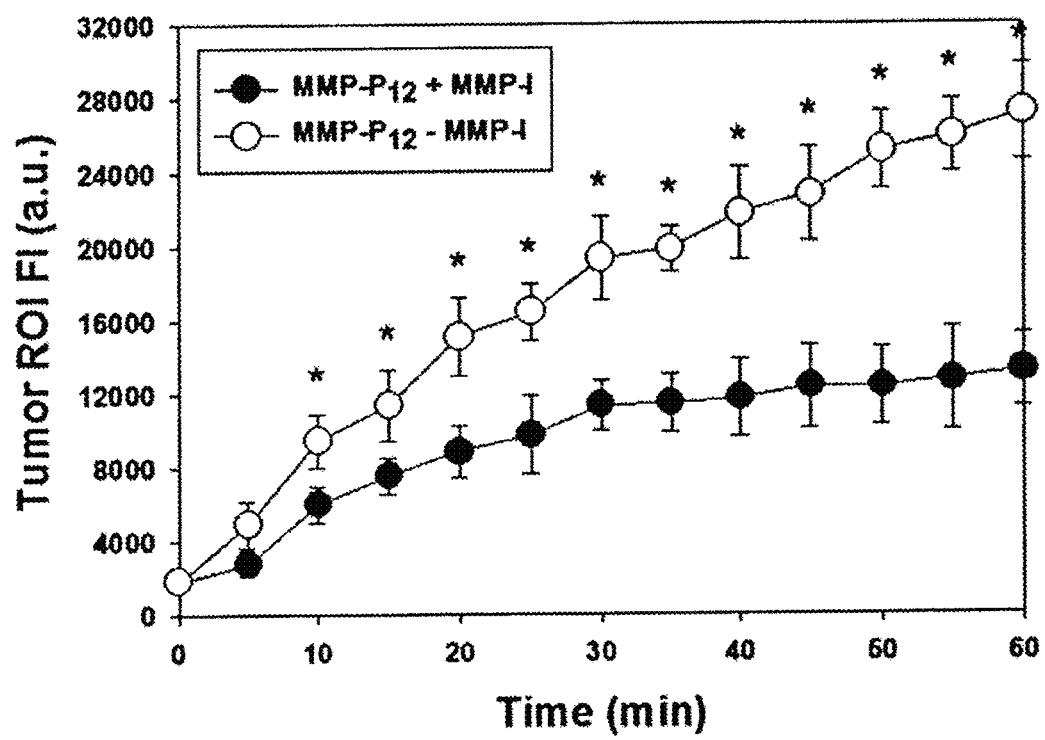

FIG. 5B is a graph of the ROI analysis of fluorescence intensity in the tumor. Data are expressed as means±s.d. (n=3). *P<0.05 (Student's t-test).

Figure 6:
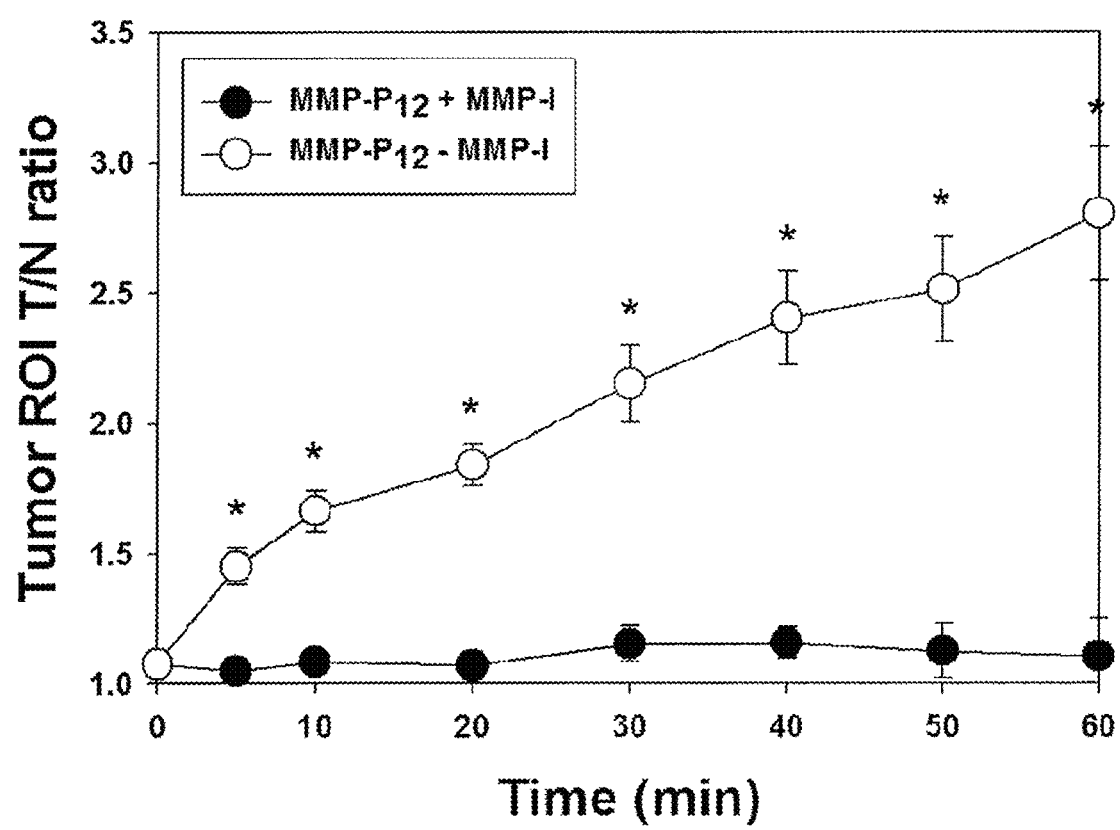

FIG. 6 is a graph depicting ROI T/N ratio analysis of fluorescence intensity in SCC7 tumors with, or without MMP-I. Data are expressed as means±s.d. (n=3). *P<0.05 (Student's t-test).

Figure 7:
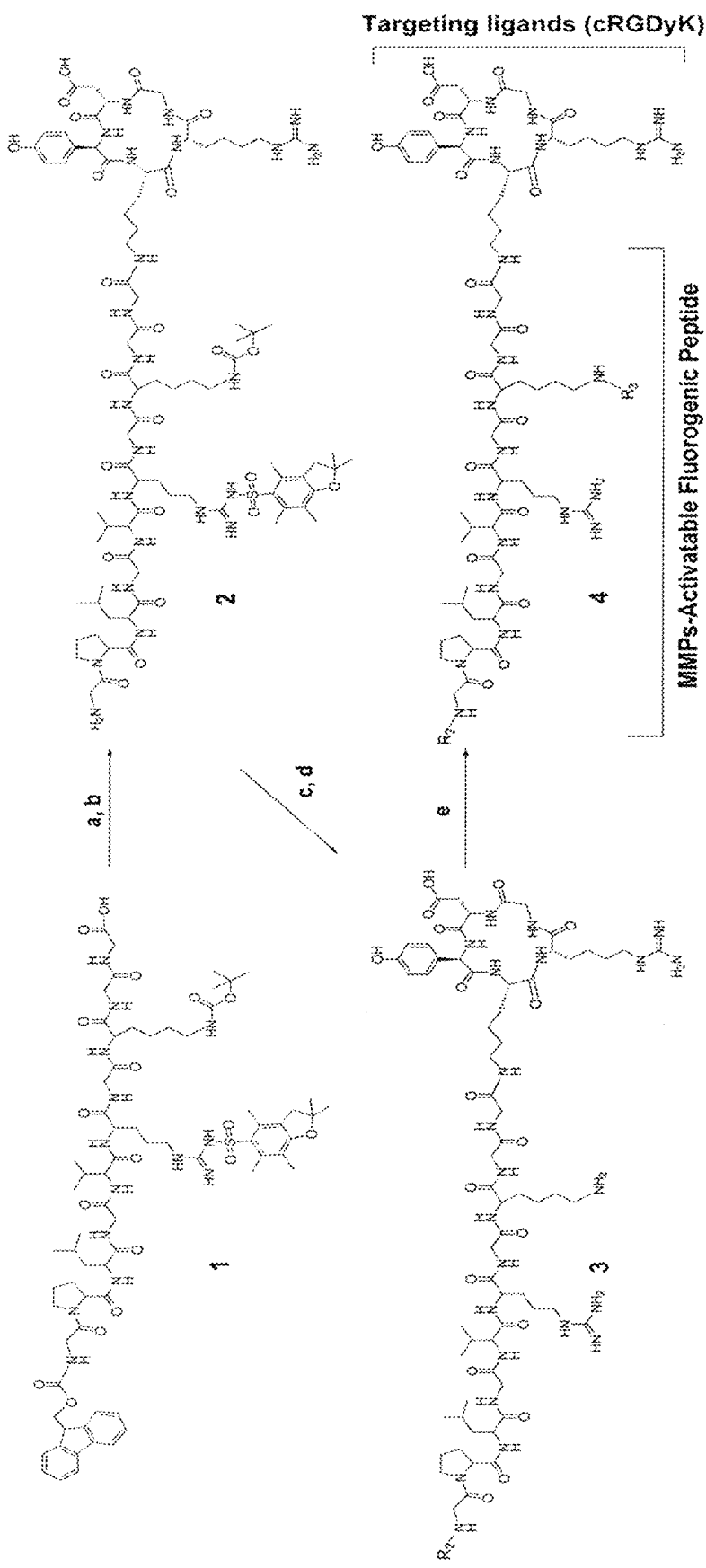

FIG. 7 is a schematic showing a general synthesis of another embodiment of the imaging agents of the present invention. The synthesis of imaging agent compound 4 is shown with the following reagents: a) HSPyU in DMF containing 2% DIPEA, c(RGDyK); b) 10% piperidine; c) Cy5.5 NHS ester in DMF containing 2% DIPEA; d) TFA/H$_2$O/TIS/EDT (85/5/5/5, v/v/v/v); e) BHQ-3 NHS ester in DMF containing 2% DIPEA.

Figure 8:
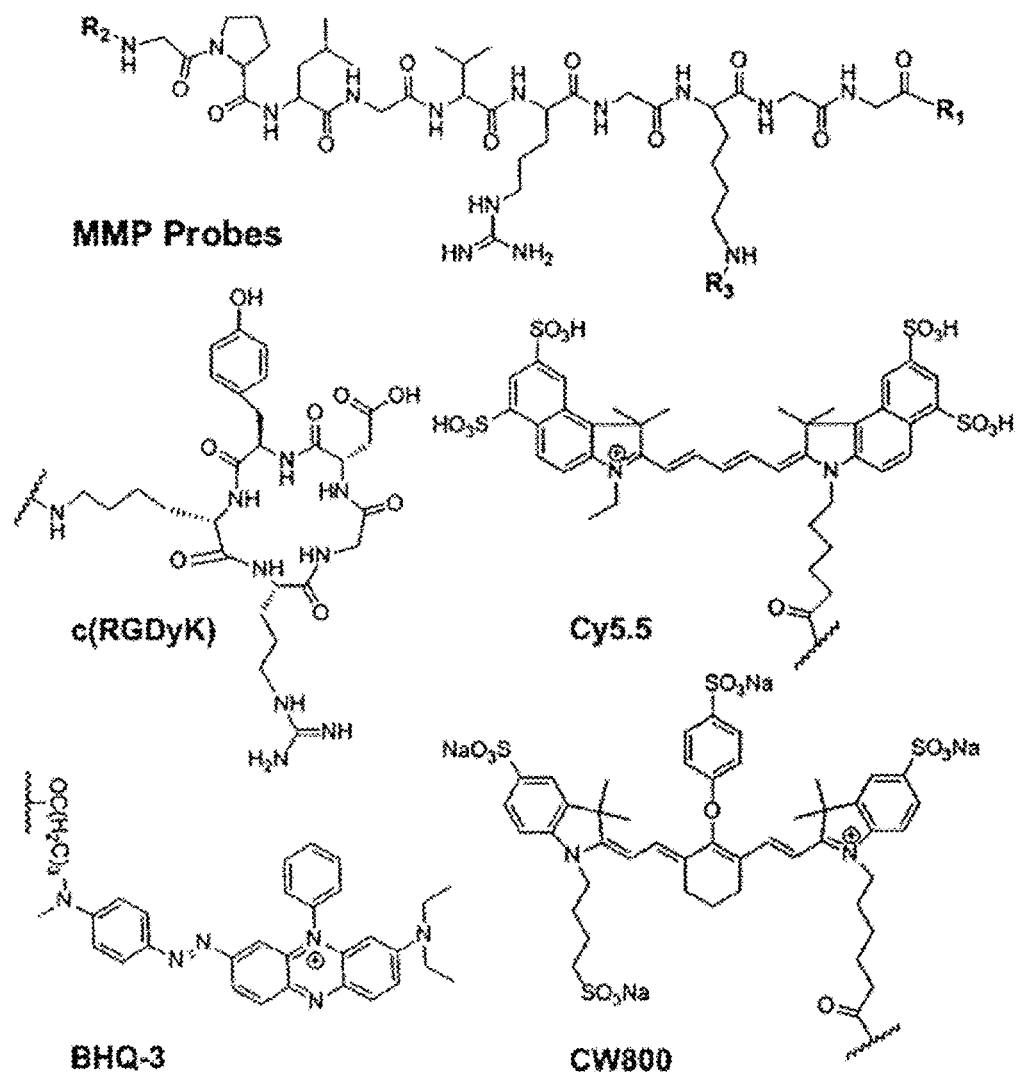

FIG. 8 depicts the chemical structures of the relevant compounds including an oligopeptide substrate, c(RGDyK), Cy5.5, BHQ-3, and CW800.

Figure 9A:
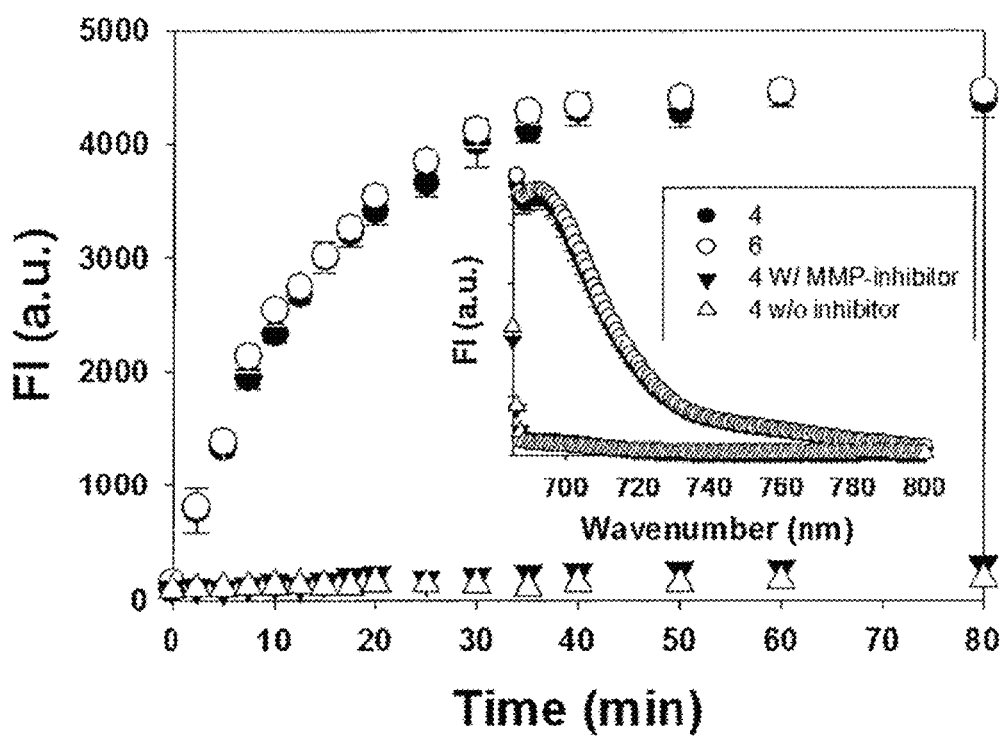
Figure 9B:
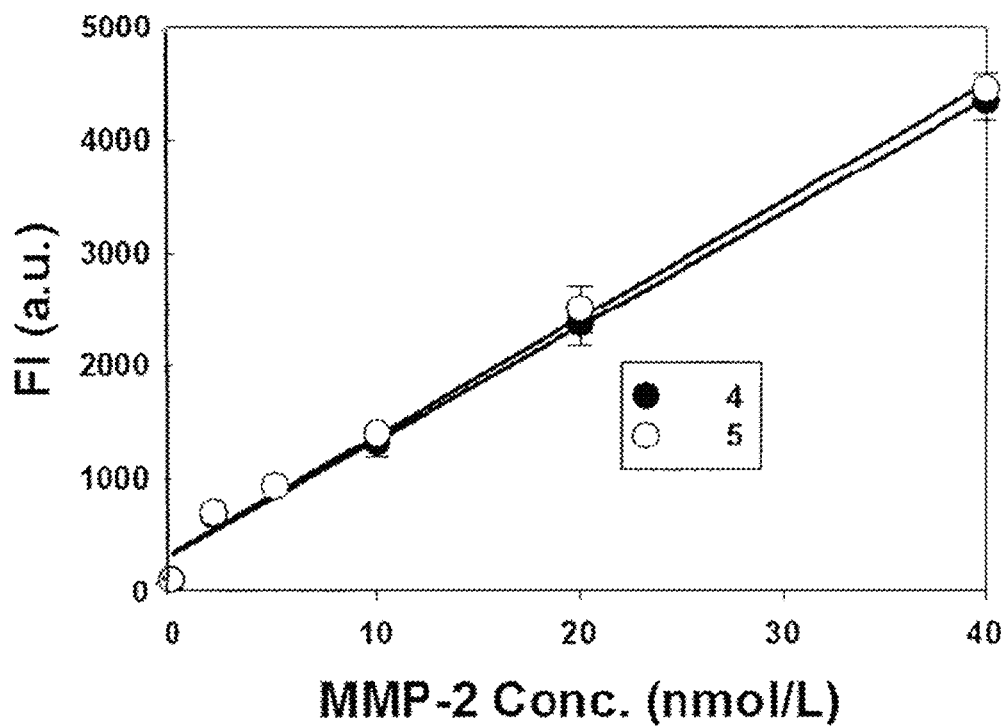

FIG. 9A shows an in vitro MMP specificity of the imaging agent MMP-P-RGD (compound 4) and MMP-6 (compound 6). The graph displays fluorescence emission kinetic spectra of the imaging agents in the presence of MMP-2 with, and without a broad-spectrum MMP inhibitor. The inset depicts fluorescence emission spectra of the probes at 80 minutes FIG. 9B is a plot showing fluorescence intensities of the imaging agents in the presence of various concentrations of activated MMP-2 (0, 2, 5, 10, 20, and 40 nM) following an 80 minute incubation. Data are expressed as mean±s.d. (n=3).

Figure 10:
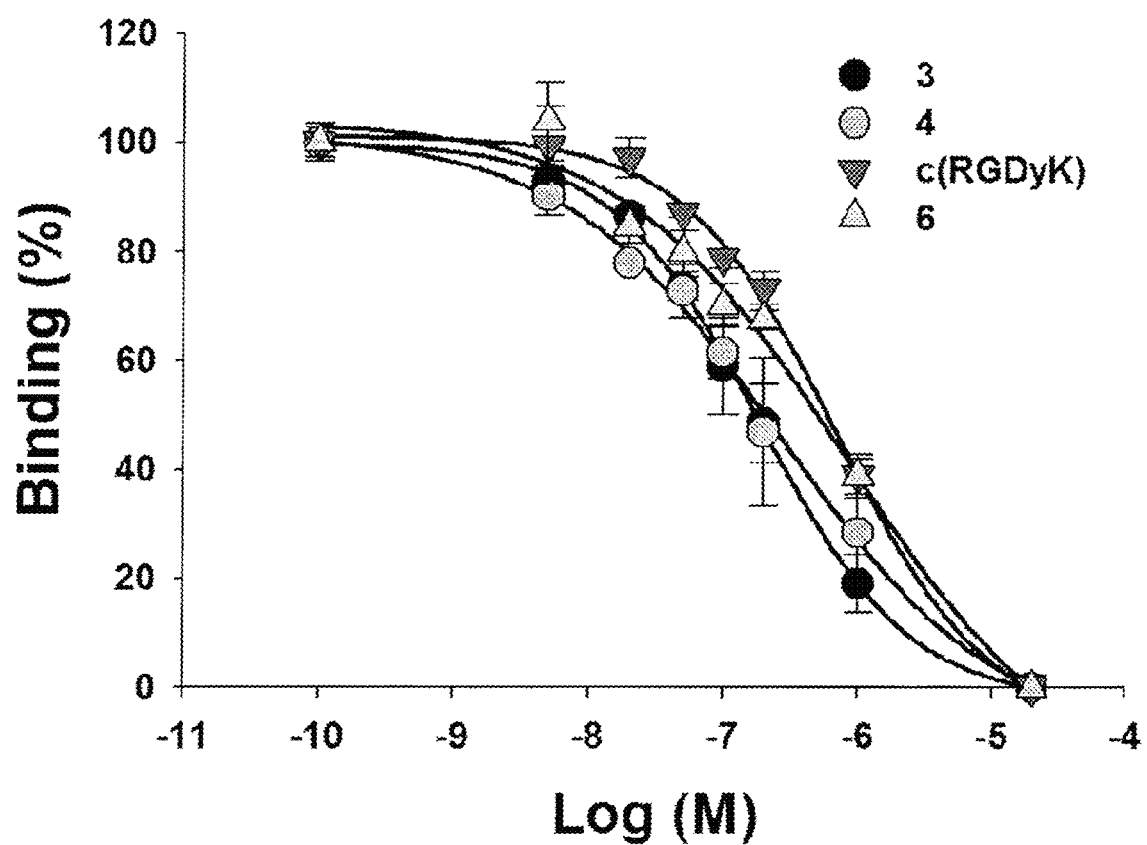

FIG. 10 is a binding competition curve for a α$_v$β3 integrin receptor assay of c(RGDyK), and compounds 4, 5, and 7 with U87MG human glioma cells. Data are expressed as mean±s.d. (n=3).

Figure 11:
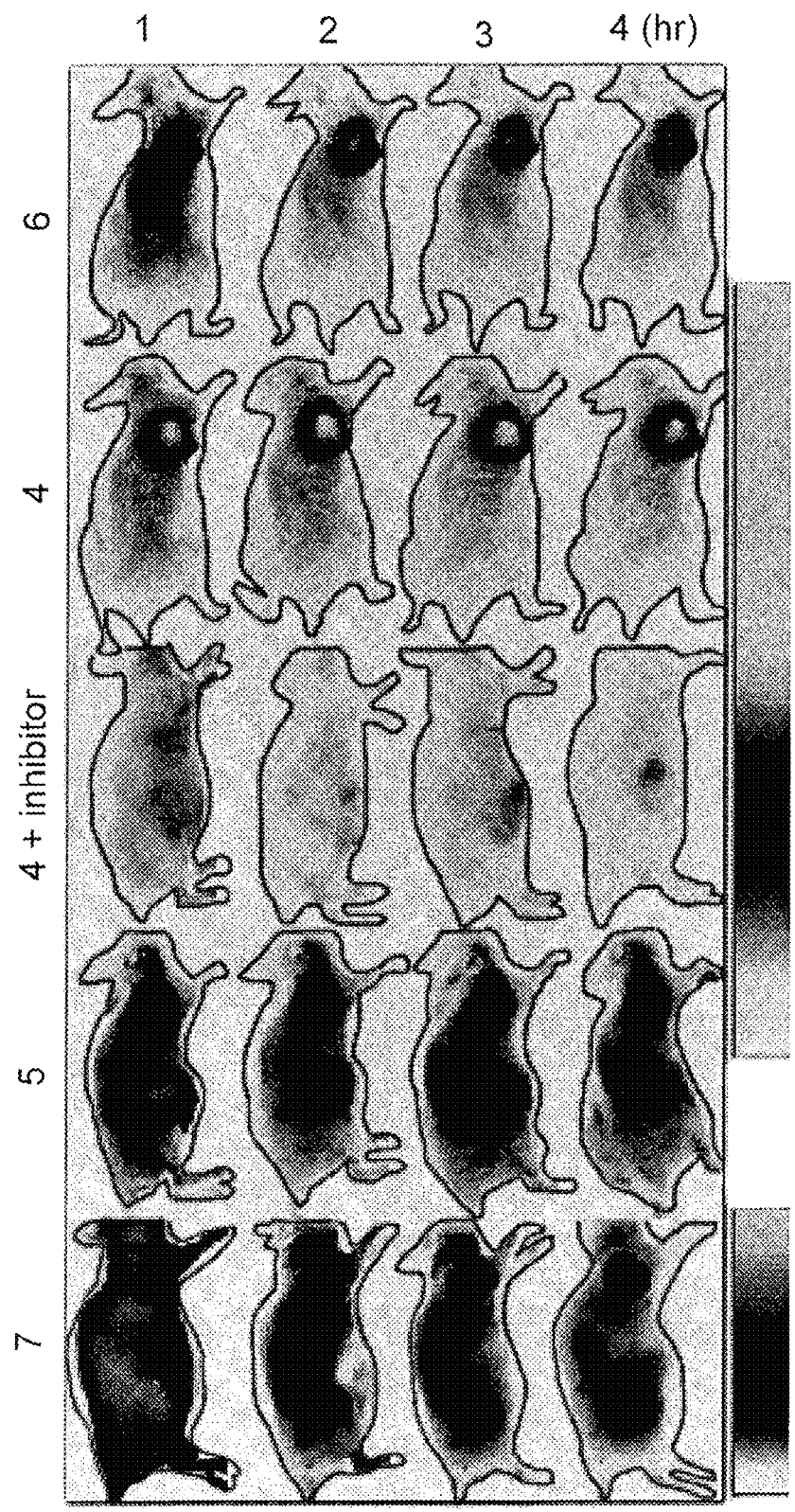

FIG. 11 depicts representative serial in vivo NIR fluorescence images of MMP- and α$_v$β3 integrin receptor-positive U87MG tumor-bearing mice injected intravenously with compounds 4, 5, 6, compound 4 with MMP inhibitor, and compound 7. Images were acquired at the indicated time points and were normalized by the maximum average value. The bar indicates radiant efficiency (upper bar; for Cy5.5, low 0, high 0.111, lower bar; for CW800, low 0, high 0.03 scaled counts/s).

Figure 12A:
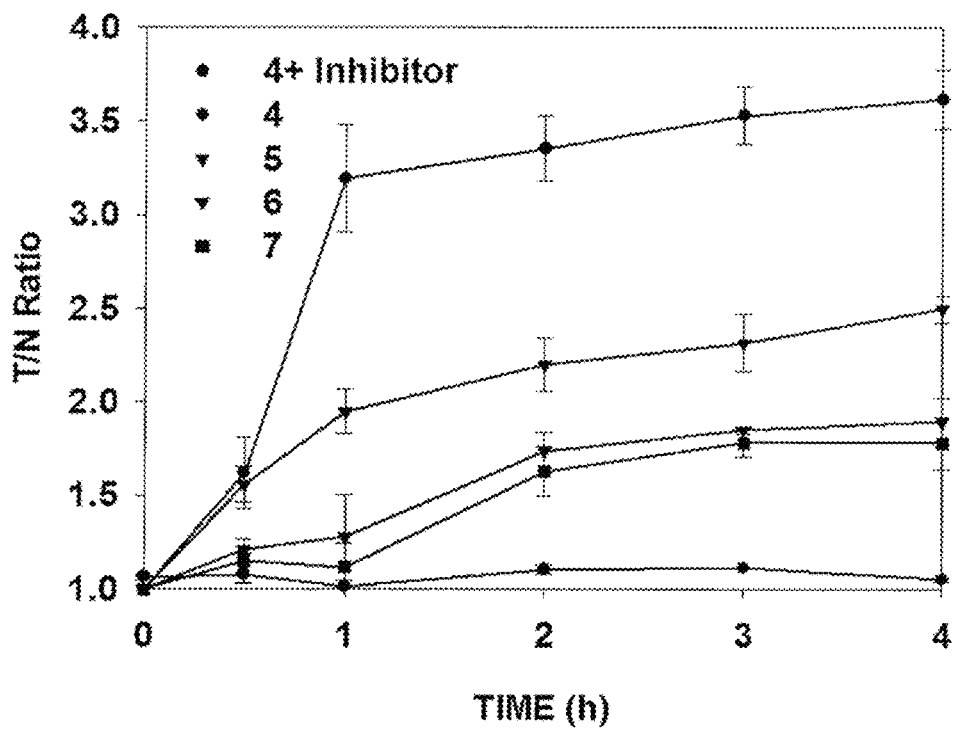

FIG. 12A is a graph depicting T/N ratio analysis of NIR fluorescence intensity of U87MG tumor in vivo.

Figure 12B:
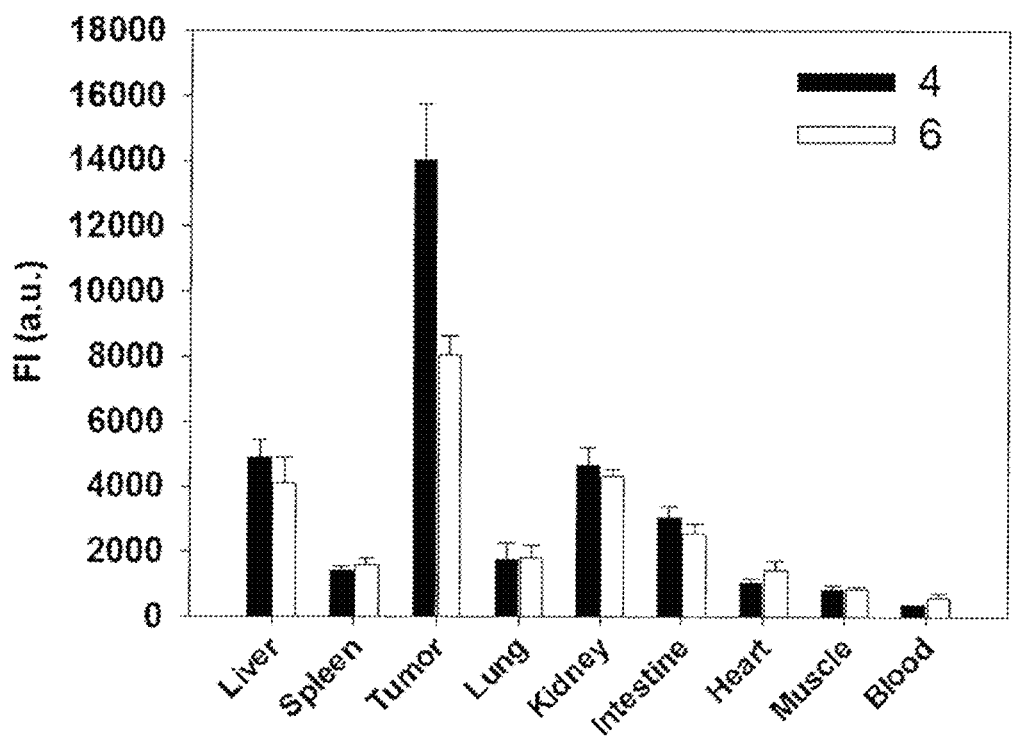

FIG. 12B is a bar graph depicting biodistribution of compounds 4 and 6 in mice. Data are expressed as mean±s.d. (n=3). * P<0.05.

Figure 13A:
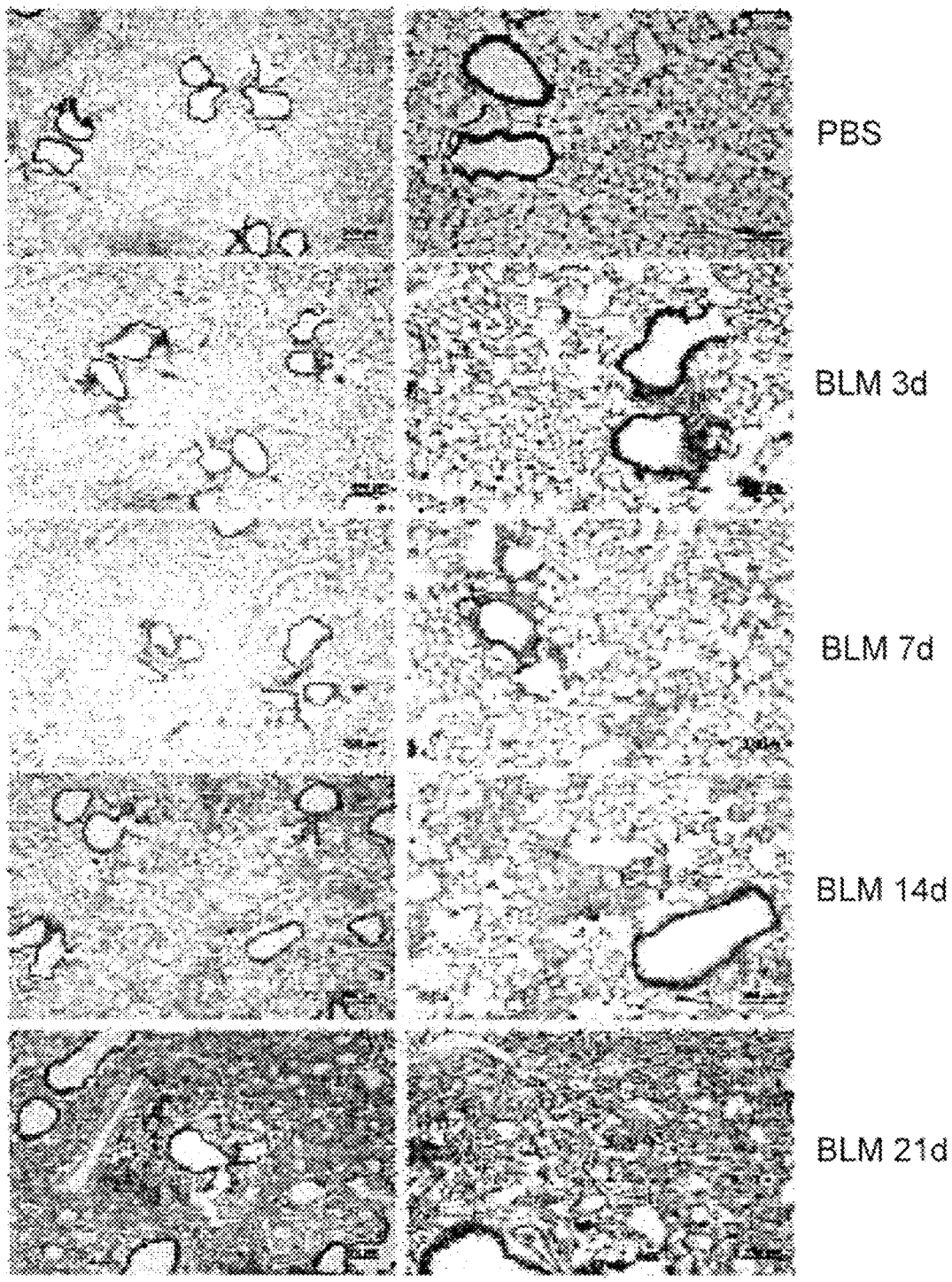

FIG. 13A depicts H&E staining of MMP-2 expression in mouse lung sections at different stages of a bleomycin-induced pulmonary fibrosis mouse model (BLM).

Figure 13B:
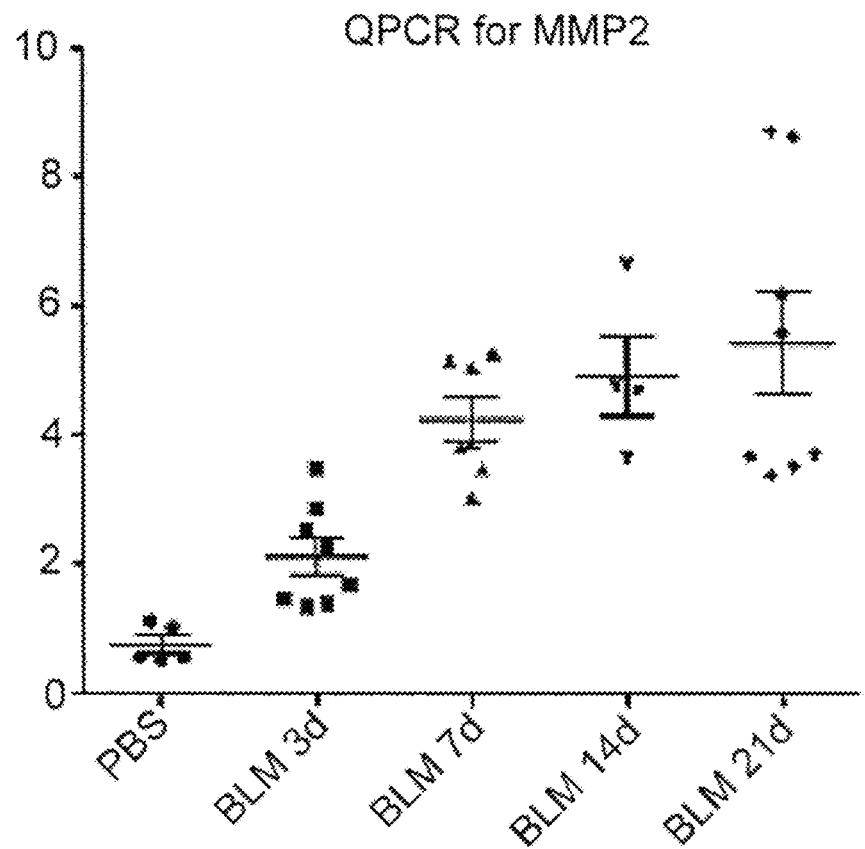

FIG. 13B depicts the amount of RT-PCR for MMP-2 in the BLM model.

Figure 13C:
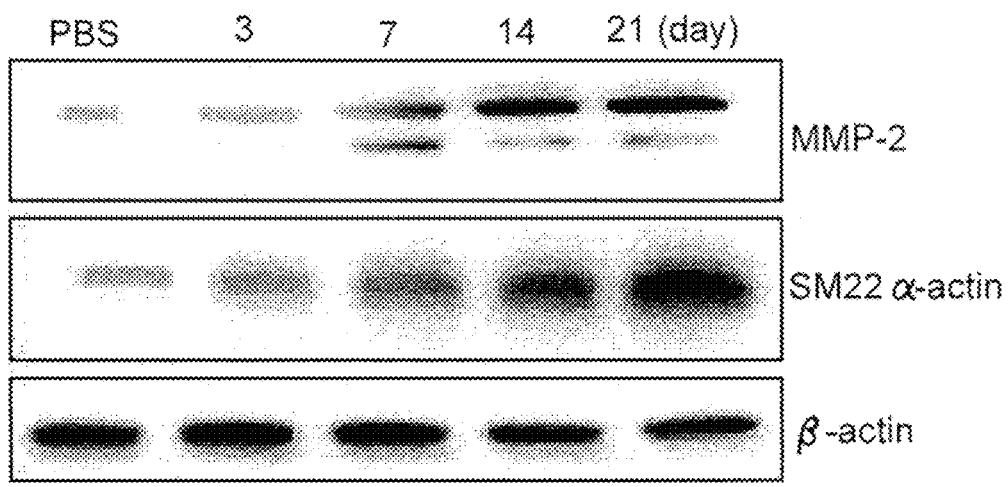

FIG. 13C depicts the Western Blot which confirms the expression of MMP-2 in the BLM model and its correlation with developmental stages of lung fibrosis.

Figure 14A:
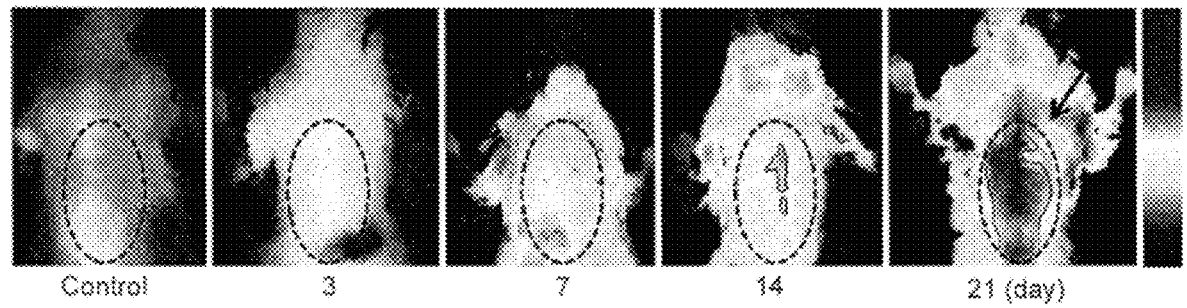

FIG. 14A is a representative serial in vivo NIR fluorescence images of BLM injected intravenously with an imaging agent of the present invention. Images were acquired at the indicated time points and were normalized by the maximum average value. The bar indicates radiant efficiency (low, 0; high, 0.063×10$^6$). Arrows indicate lung regions.

Figure 14B:
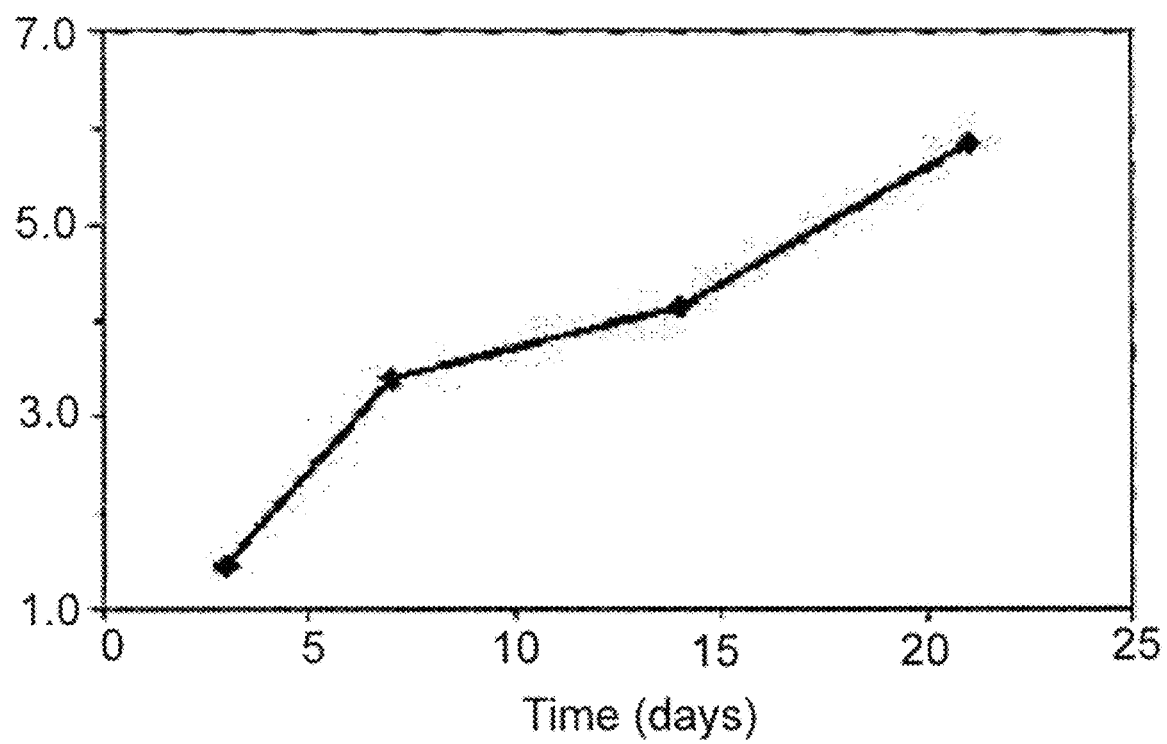

FIG. 14B is a graph depicting normalized signal in the ROI of the BLM lung compared to that of control, at day 0.

Figure 15A:
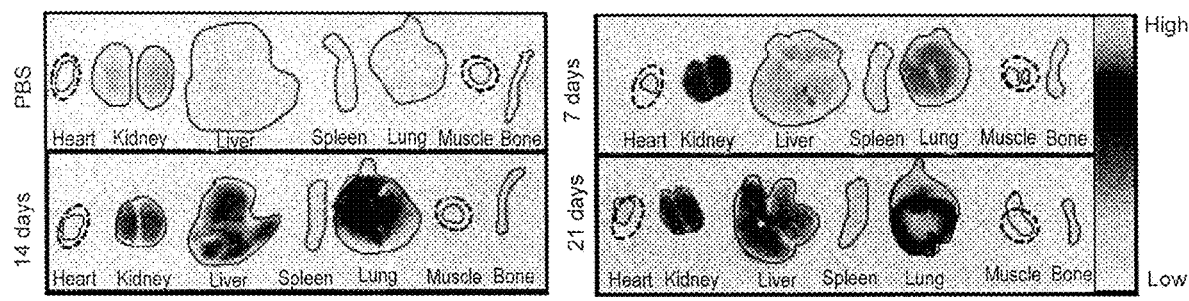

FIG. 15A depicts images of dissected organs of the BLM after intravenous injection of the agent of the present invention. The bar indicates radiant efficiency (low, 0; high, 0.074×10$^6$).

Figure 15B:
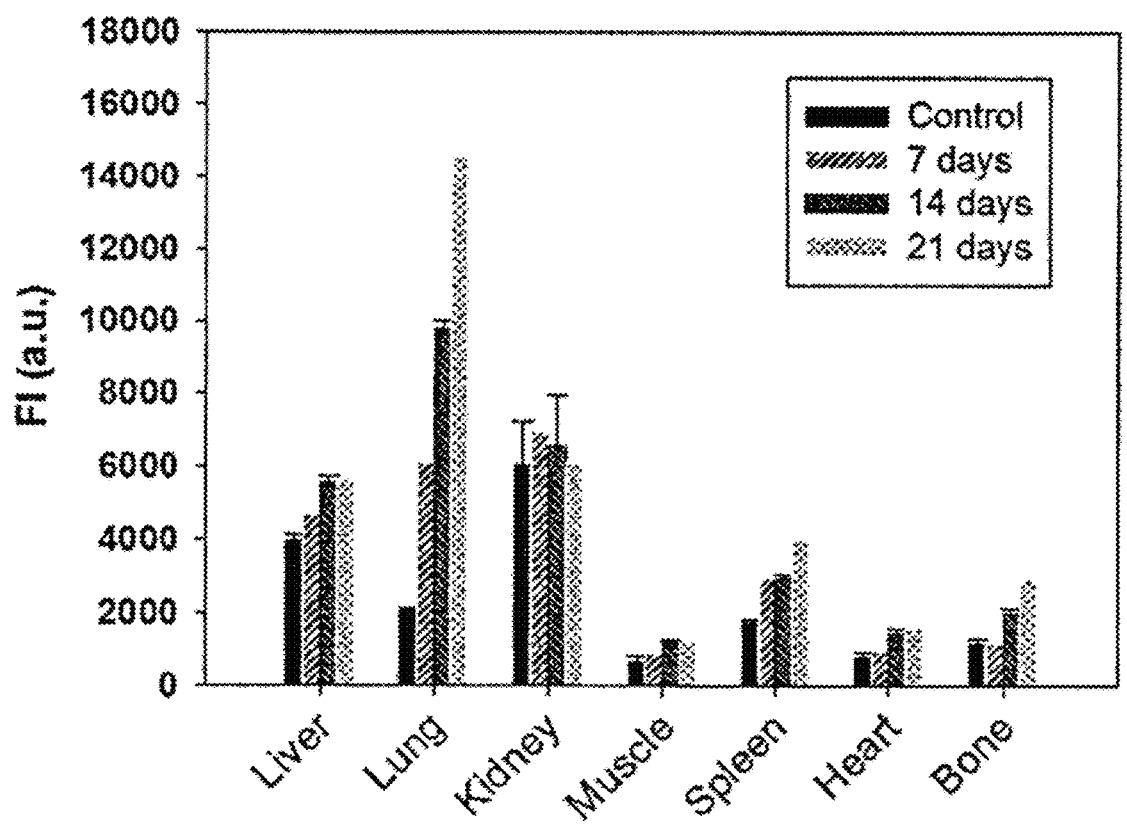

FIG. 15B is a bar graph depicting the biodistribution of the activated agent of an embodiment of the present invention.

Figure 16A:
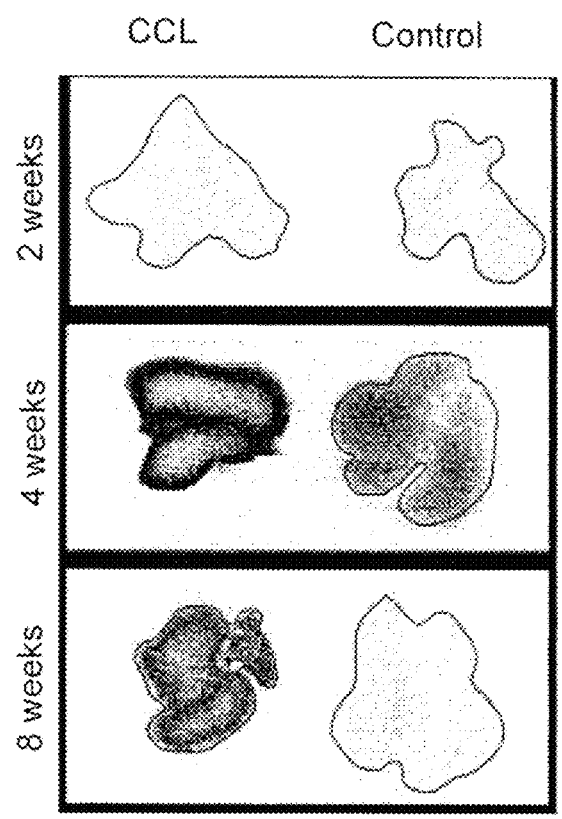

FIG. 16A are representative images of dissected livers of CCl$_4$-treated mice sacrificed at 4 hours after intravenous injection of the agent of an embodiment of the present invention.

Figure 16B:
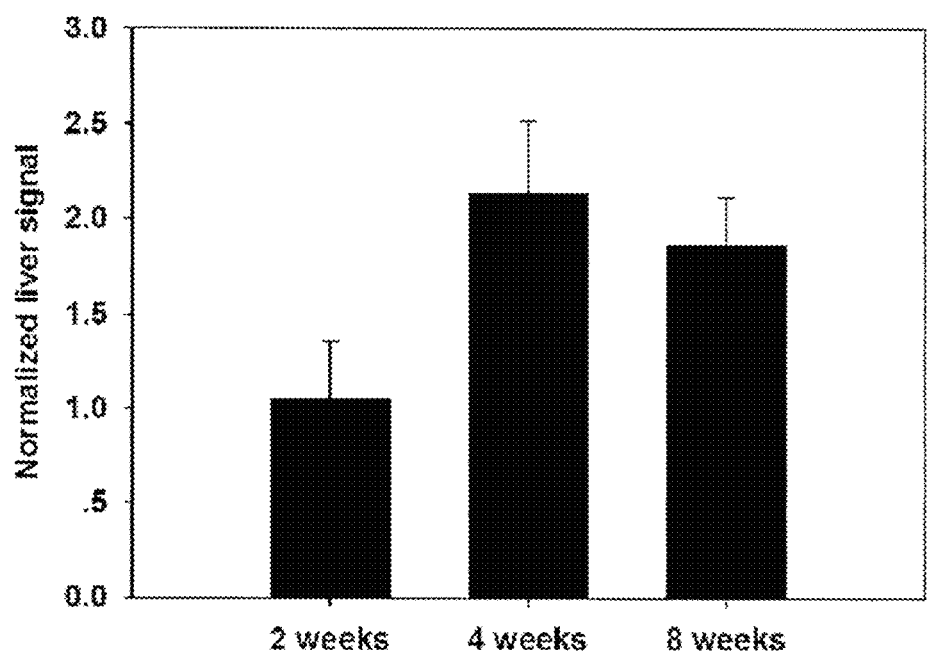

FIG. 16B is a bar graph depicting the normalized signal in the ROI of the liver compared to that of control.

Figure 17A:
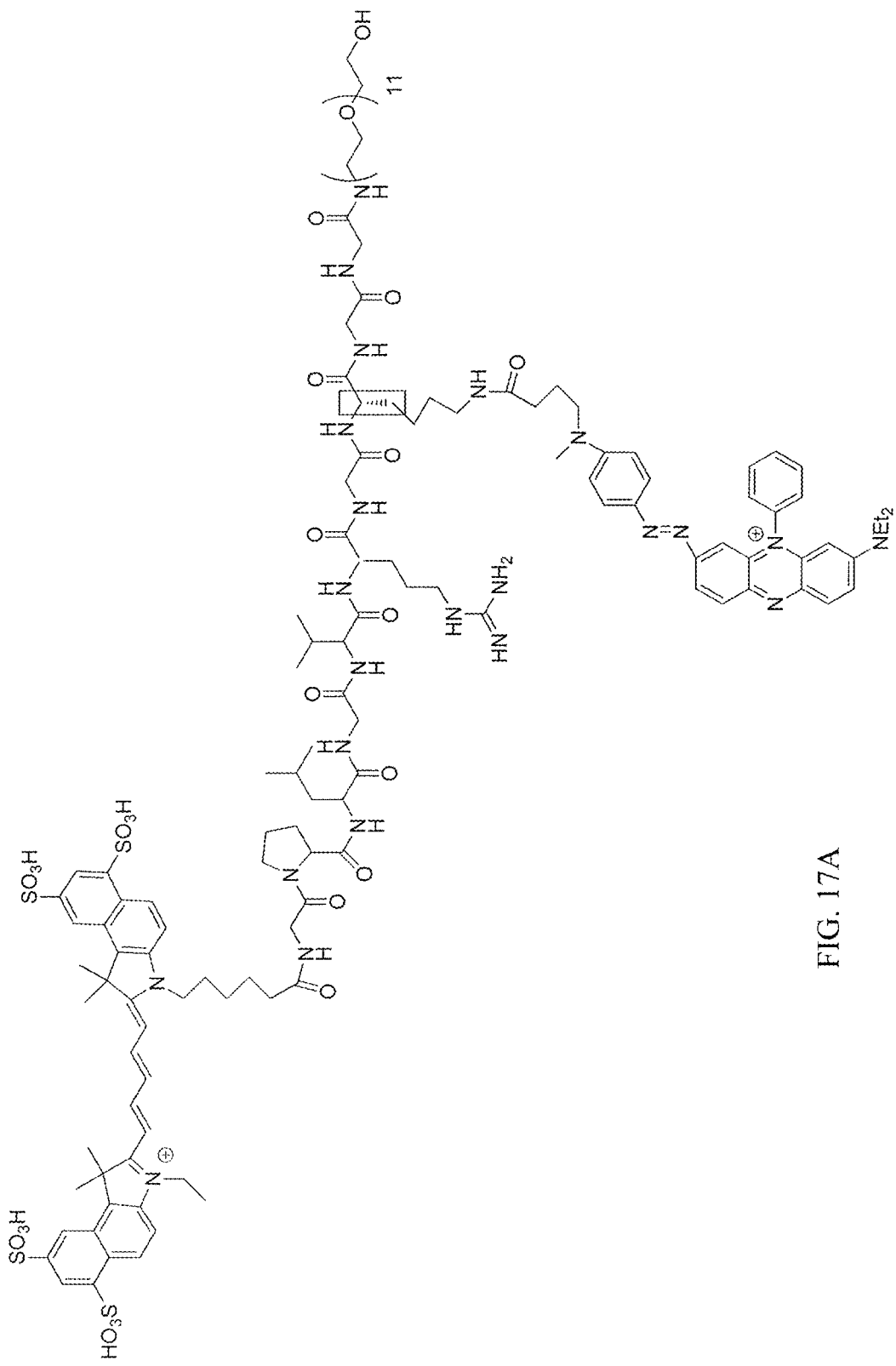

FIG. 17A depicts the structure of L-MMP-P12.

Figure 17B:
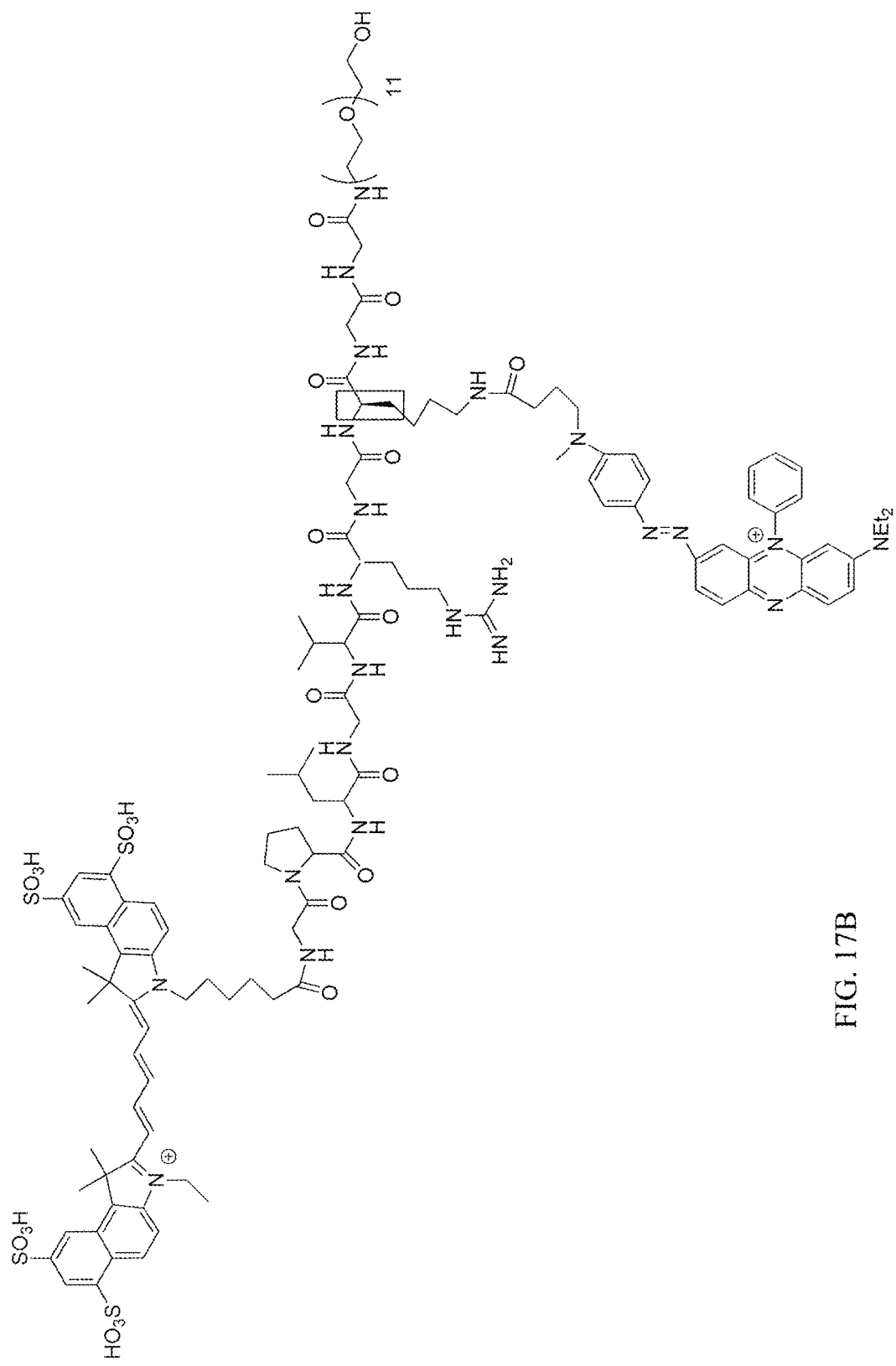

FIG. 17B depicts the structure of D-MMP-P12.

Figure 18A:
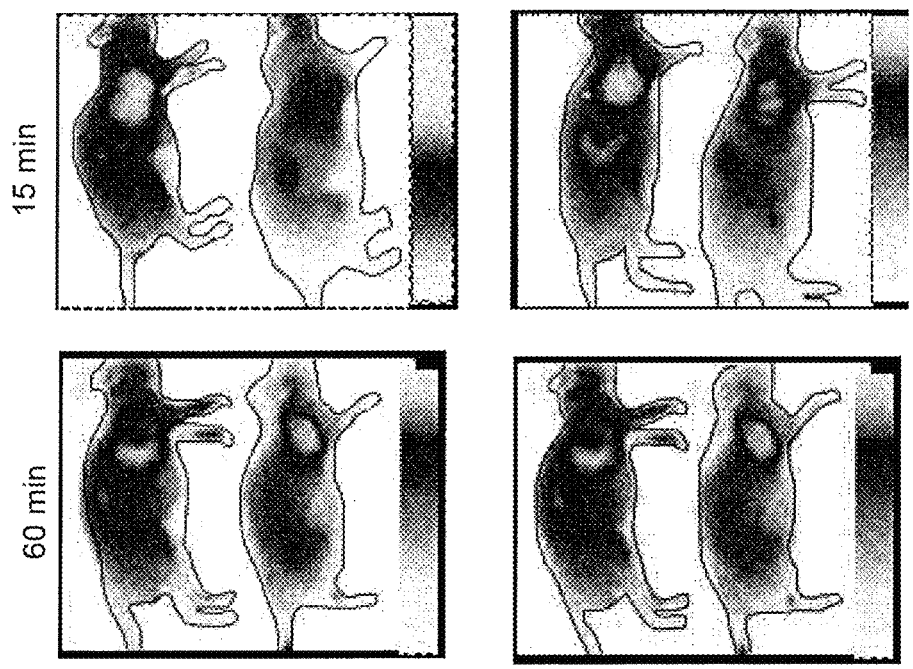

FIG. 18A depicts representative serial in vivo NIR fluorescence images of MMP- and α$_v$β3 integrin receptor-positive SCC7 tumor-bearing mice injected intravenously with L-MMP-P12 and D-MMP-P12. Images were acquired at the indicated time points and were normalized by the maximum average value. The bar indicates radiant efficiency (upper bar; for Cy5.5, low 0, high 0.111, lower bar; for CW800, low 0, high 0.03 scaled counts/s).

Figure 18B:
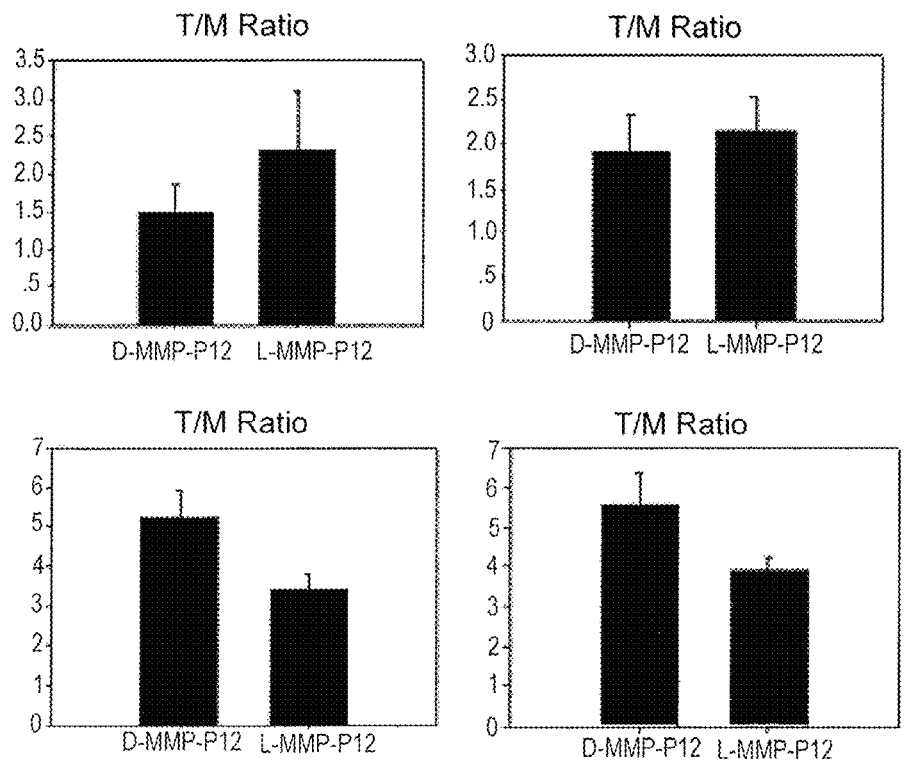

FIG. 18B depicts region of interest analysis of SCC7 tumors at indicated time points postinjection of L-MMP-P12 or D-MMP-P12.

Figure 19A:
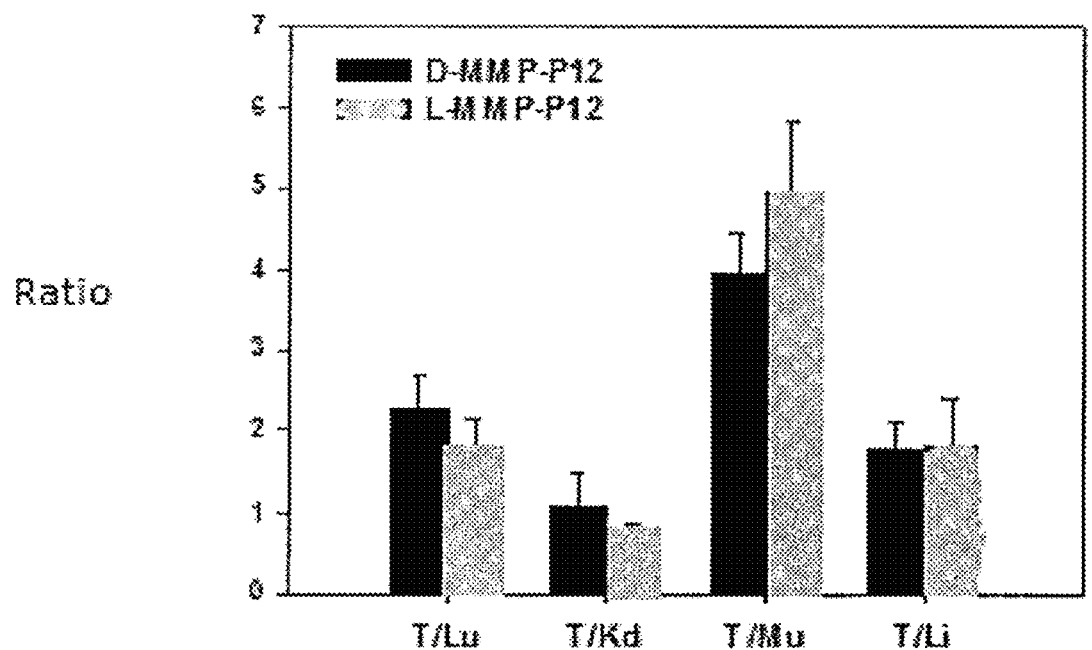
Figure 19B:
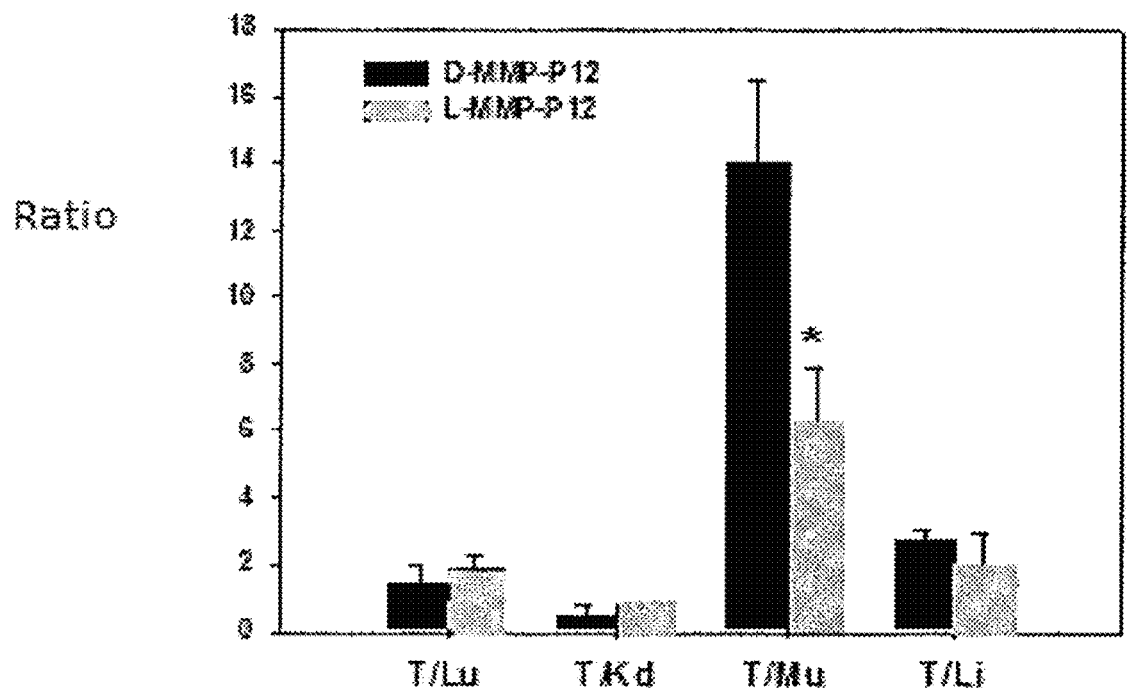

FIGS. 19A and 19B are bar graphs depicting the ratio of tumor signals versus other major organs of D-MMP-P12 and L-MMP-P12 in SCC7 tumor-bearing mice at 30 min (FIG. 19A) and 120 min (FIG. 19B). Data are expressed as mean±s.d. (n=3). * P<0.05. T=tumor; Lu=lung; Kd=kidney; Mu=muscle, Li=liver.

Figure 20A:
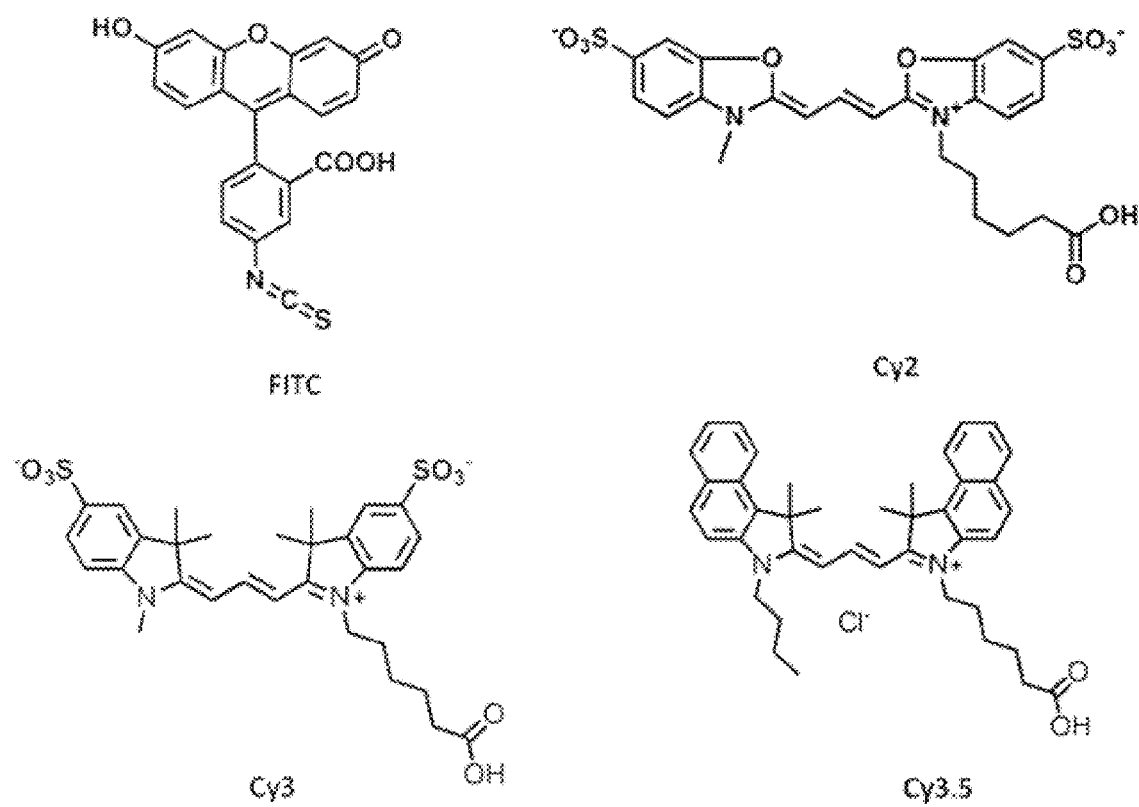

FIG. 20A depicts the structures of the optical dyes fluorescein isothiocyanate ("FITC"), Cy2, Cy3, and Cy 3.5.

Figure 20B:
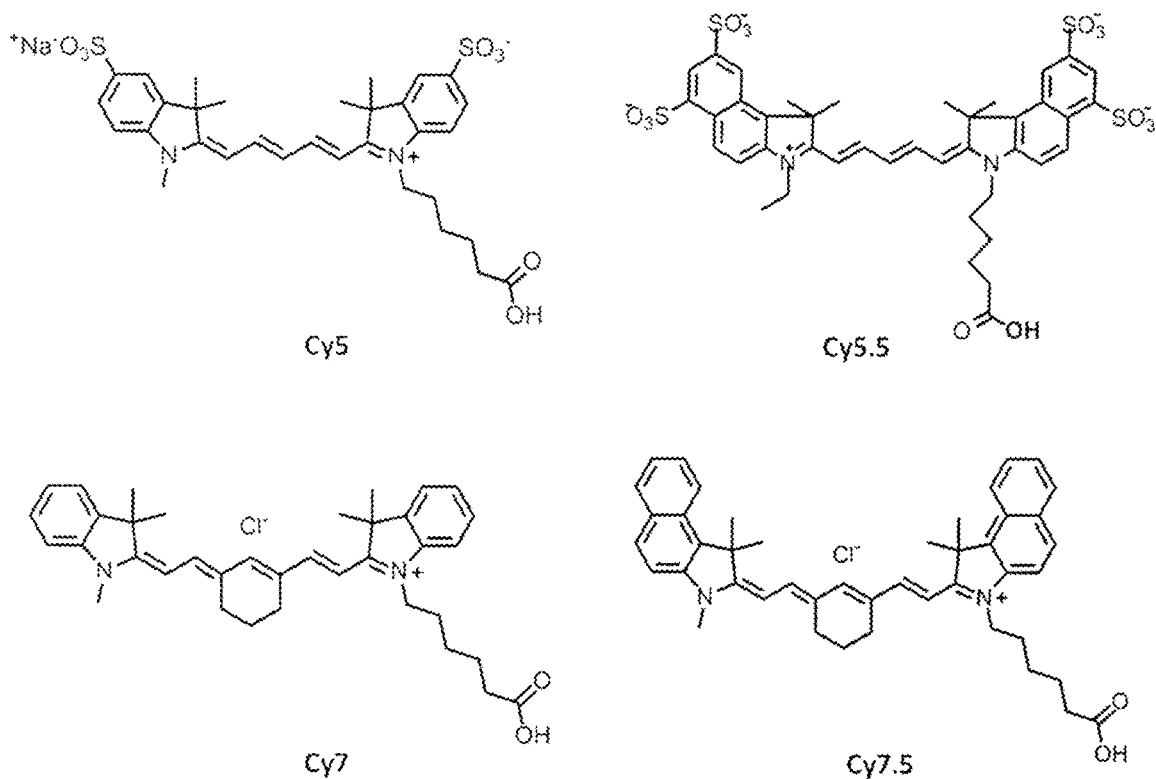

FIG. 20B depicts the structures of the optical dyes Cy5, Cy5.5, Cy7, and Cy7.5.

Figure 20C:
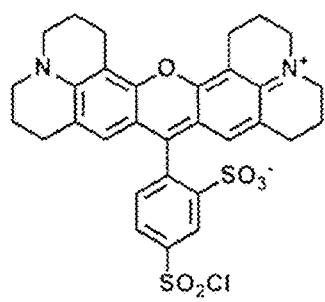
Figure 20C:
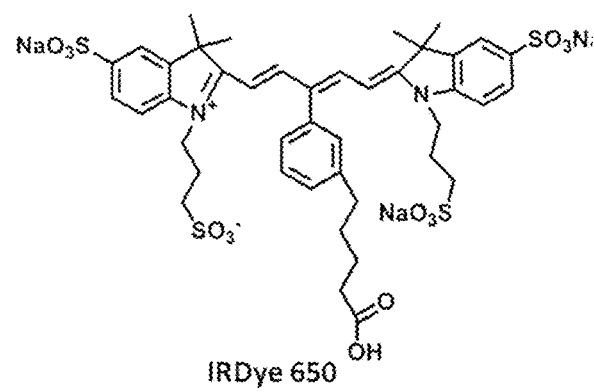
Figure 20C:
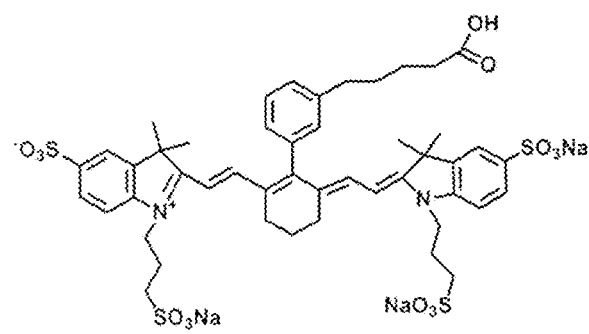
Figure 20C:
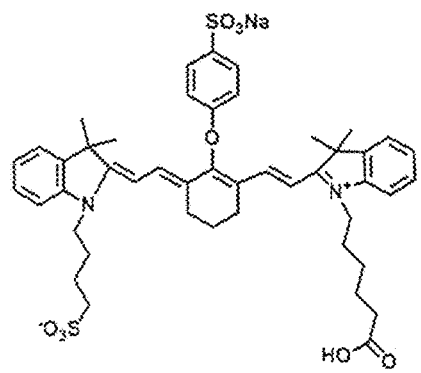

FIG. 20C depicts the structures of the optical dyes Texas Red, IRDye 650, IRDye 750, and IRDye 800.

Figure 21A:
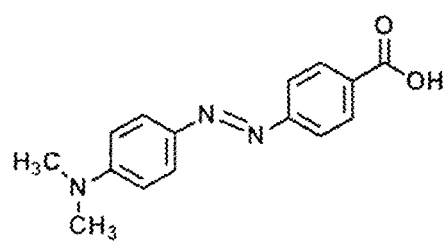
Figure 21A:
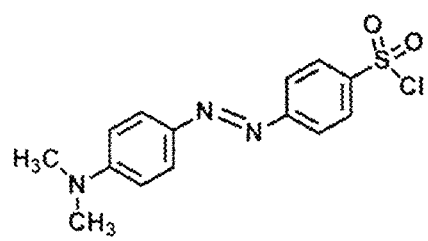
Figure 21A:
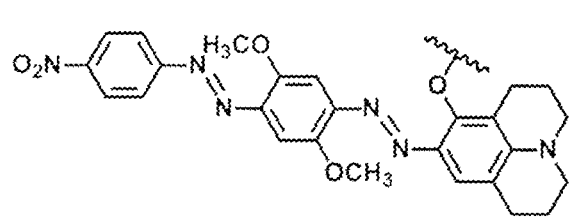
Figure 21A:
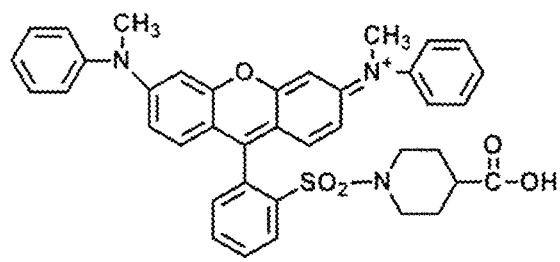

FIG. 21A depicts the structures of the quenchers DABCYL, DABSYL, Blackberry Quencher 650, and QSY™ 7.

Figure 21B:
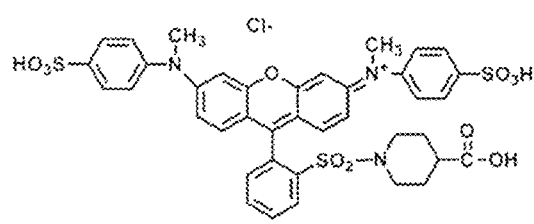
Figure 21B:
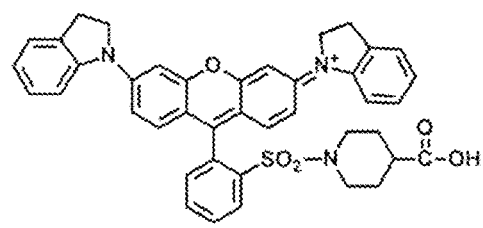
Figure 21B:
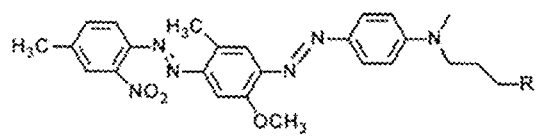
Figure 21B:
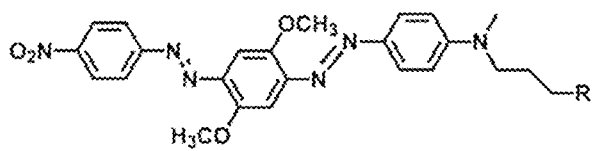

FIG. 21B depicts the structures of the quenchers QSY™ 9, QSY™ 21, BHQ1, and BHQ2.

Figure 21C:
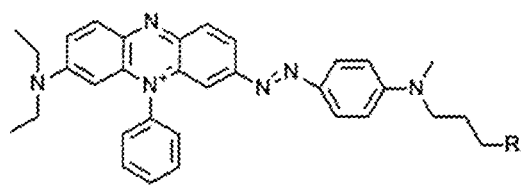
Figure 21C:
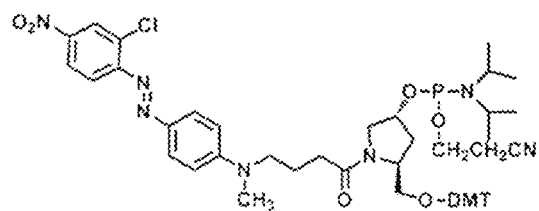
Figure 21C:
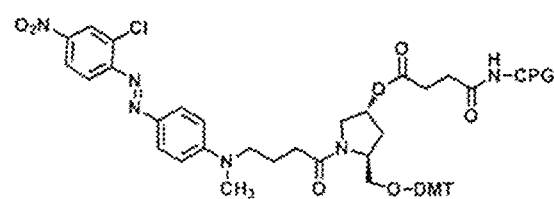

FIG. 21C depicts the structures of the quenchers BHQ3, Eclipse quencher phosphoramidite, and Eclipse quencher CPG.

DETAILED DESCRIPTION OF THE INVENTION

In accordance with an embodiment, the invention provides quenched molecular beacons with a polyethylene glycol (PEG) or a derivative thereof or a targeting ligand that is useful as an ultra-efficient optical imaging agents for imaging various protease activities in vivo.

In an embodiment, the present invention provides one or more imaging agents having the following Formula I:

wherein:
F is a near infrared fluorophore;
S is an enzymatically cleavable oligopeptide;
Q is a fluorescence quencher molecule; and
M is a moiety selected from the group consisting of PEG or a derivative thereof and a targeting ligand, wherein the PEG (polyethylene glycol) or derivative thereof, and wherein F, Q and M are linked to separate amino acids of the enzymatically cleavable oligopeptide. In an embodiment (1) the PEG derivative does not have a terminal $CH_3O$ group, and (2) the targeting ligand is not biotin.

In another embodiment, the present invention provides one or more imaging agents of formula I, as set forth above, wherein M is PEG or derivative thereof.

In accordance with a further embodiment, the present invention provides one or more imaging agents of formula I, as set forth above, wherein the terminal chain end of the polyethylene glycol derivative can be carboxyl, carboxy alkyl, alkoxy, alkoxyalkyl, alkoxy alkoxy, hydroxyalkoxy, acetoxy, acetoxy alkoxy, amido, amino, or carbonato. In an embodiment, the terminal chain end of the polyethylene glycol polymer molecule cannot include a methoxy group.

The PEG or derivative thereof can have any suitable molecular weight, for example, a number average molecular weight of 10,000 or less, 5,000 or less, 3,000 or less, 2,000 or less. In an embodiment, the PEG or derivative thereof has a molecular weight between about 60 Daltons to about 1200 Daltons. In another embodiment, the PEG or a derivative thereof has a number average molecular weight less than 1200 Daltons, or between about 100 to about 1200 Daltons, including, for example, 104, 148, 192, 236, 280, 324, 368, 412, 456, 500, 544, 588, 632, 676, 720, 764, 808, 852, 896, 940, 984, 1028, 1072, 1116, 1160, and 1200 Daltons.

In a further embodiment, the present invention provides one or more imaging agents of formula I, as set forth above, wherein M is a targeting ligand.

In another embodiment, the present invention provides one or more imaging agents of formula I, as set forth above, wherein M is a targeting ligand which can include, but is not limited to cytokines, chemokines, growth factors, such as interferons, erythropoietin (EPO), TNFα, interleukins, growth hormone, granulocyte colony stimulating factor (G-CSF), granulocyte macrophage colony stimulating factor (GM-CSF); gonadotropins, insulin and other hormones; integrins; immunoglobulins (e.g., polyclonal, monoclonal, chimeric, humanized or single chain, fragments, etc.), peptides and other proteins that interact with a cell surface molecule or with a pattern recognition receptor, however the targeting ligand cannot include biotin.

In still a further embodiment, the present invention provides one or more imaging agents of formula I, as set forth above, wherein M is a targeting ligand which can include the class of tumor receptor binding molecules (comprised of peptides or small molecules) including, but not limited to, integrins, somatostatin, bombesin, neurotensin, cholesytekinin, ST, estrogen, and progesterone receptor binding compounds.

In yet another embodiment, the present invention provides one or more imaging agents of formula I, as set forth above, wherein M is a targeting ligand which can include the class of molecules involved in vascular lesions, including, but not limited to, integrins, selectins, vascular endothelial growth factor, fibrins, tissue plasminogen activator, thrombin, LDL, HDL, Sialyl Lewis$^x$ and its mimics, and atherosclerotic plaque binding compounds.

In yet another embodiment, the present invention provides one or more imaging agents of formula I, as set forth above, wherein M is the targeting ligand cyclic Arg-Gly-Asp (SEQ ID NO: 1) comprising peptide c(RGDyK) or Arg-Gly-Asp-Tyr-Lys (SEQ ID NO: 2).

In an embodiment, the present invention provides one or more imaging agents of formula I, as set forth above, wherein M is chemically linked, e.g., covalently, either directly or indirectly to a separate amino acid of the enzymatically cleavable oligopeptide. For example, the targeting ligand can be attached to the probe by the substrate's N-terminal amine group, C-terminal carboxylic group, or any reactive group provided by the side chain of an amino acid residues with the substrate such as sulkdryl group provided by a cysteine.

In an embodiment, the present invention provides one or more imaging agents of formula I, as set forth above, wherein F is chemically linked either directly or indirectly to a separate amino acid of the enzymatically cleavable oligopeptide.

In another embodiment, the present invention provides one or more imaging agents of formula I, as set forth above, wherein F comprises a near infrared fluorescent dye.

In a further embodiment, F can include suitable fluorophores(chromes) can include, but without limitation fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience, Piscataway, N.J.), IRDyes® (Li-Cor, Lincoln, Nebr.), Alexa Fluors (Molecular Probes Inc., Eugene, Oreg.), HILYTE™

Fluors (AnaSpec, Fremont, Calif.), DYLITE™ Fluors (Pierce, Inc., Rockford, Ill.), and Flamma™ Fluors (BioActs, Layfayette, Ind.).

In yet another embodiment, the present invention provides one or more imaging agents of formula I, as set forth above, wherein, F is selected from the group consisting of Cy5.5, Cy7, Cy7.5, IRDye800CW and their derivatives.

In a further embodiment, the present invention provides one or more imaging agents of formula I, as set forth above, wherein F is Cy5.5.

The structures of the dyes are depicted in FIGS. 20A-20C.

In an embodiment, the present invention provides one or more imaging agents of formula I, as set forth above, wherein S includes any reported protease substrate that is specifically recognized and degraded by a target protease or protease of interest.

In accordance with the present invention, S can comprise, consisting essentially of, or consisting of, any length oligopeptide such that a fluorophore, a quencher and a PEG or derivative thereof or a targeting molecule can be attached, and wherein the oligopeptide includes an amino acid sequence cleaved by a protease of interest which is located between the fluorophore and the quencher.

In a further embodiment, the present invention provides one or more imaging agents of formula I, as set forth above, wherein S comprises an amino acid sequence cleavable by a protease, non-limiting examples of which are selected from the group consisting of: Arg-C proteinase, Asp-N endopeptidase, chymotrypsin-high specificity, chymotrypsin-low specificity, clostripain, enterokinase, Factor Xa, glutamyl endopeptidase, granzyme B, LysC, pepsin (pH 1.3), pepsin (pH>2), proline-endopeptidase, proteinase K, staphylococcal peptidase I, thermolysin, thrombin, and matrix metalloproteinases (MMPs, a family of zinc-dependent proteins that play essential roles in many aspects of biology, including cell proliferation, differentiation, apoptosis, and migration through degradation of matrix). Expressions of MMPs are significantly involved in cancer progression and certain inflammatory diseases. As such, S may also comprise an amino acid sequence cleaved by a protease selected from the group consisting of: MMP-1, MMP-2, MMP-3, MMP-4, MMP-5, MMP-6, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27, MMP-28, MMP-29, and MMP-30, caspase-1, caspase-2, caspase-3, caspase-4, caspase-5, caspase-6, caspase-7, caspase-8, caspase-9, caspase-10, caspase-11, caspase-12, caspase-13, caspase-14, cathepsin-B, cathepsin-C, cathepsin-D, cathepsin-E, cathepsin-G, cathepsin-H, and cathepsin-L, and dipeptidyl peptidase.

In yet another embodiment, the present invention provides one or more imaging agents of formula I, as set forth above, wherein S is a substrate for a MMP selected from the group consisting of MMP-1, MMP-2, MMP-3, MMP-4, MMP-5, MMP-6, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27, MMP-28, MMP-29, and MMP-30.

In another embodiment, the present invention provides one or more imaging agents of formula I, as set forth above, wherein S is an enzymatically cleavable oligopeptide having between, for example, 3 and 100 amino acids in length, 4 and 100 amino acids in length, between 3 and 50 amino acids in length, between 5 and 30 amino acids in length, between 5 and 25 amino acids in length, between 5 and 20 amino acids in length, or between 5 and 10 amino acids in length.

In a further embodiment, the present invention provides one or more imaging agents of formula I, as set forth above, wherein S is an enzymatically cleavable oligopeptide oligopeptide comprising an amino acid sequence motif cleavable by the proteases described herein.

In another embodiment, the present invention provides one or more imaging agents of formula I, as set forth above, wherein S is an oligopeptide comprising an enzymatically cleavable amino acid sequence motif selected from the group consisting of Gly-Pro-Leu-Gly-Val-Arg-Gly-Lys (MMP2) (SEQ ID NO: 3), Val-Pro-Leu-Ser-Leu-Thr-Met (MMP7) (SEQ ID NO: 4), Pro-Tyr-Ala-Leu-Trp-Ala (MMP1) (SEQ ID NO: 5), Pro-Leu-Ala-Tyr-Trp-Ala-Arg (MMP8) (SEQ ID NO: 6), Leu-Pro-Lys-Gly-Leu (MMP-1, MMP-2, MMP-7, MMP-8, MMP-9, MMP-12, MMP-13, MMP-14, MMP-15, MMP-16, ADAM10, ADAM17/TACE, Cathepsin D, and Cathepsin E) (SEQ ID NO: 7), Arg-Pro-Lys-Pro-Val-Glu (MMP-3, MMP-10, Trypsin, HGF) (SEQ ID NO: 8), Val-Pro-Arg (Kallikrein 4, Kallikrein 5, Kallikrein 8, Kallikrein 13, Kallikrein 14, and MASP3) (SEQ ID NO: 9).

In accordance with the present invention, in an embodiment, the present invention provides one or more imaging agents of formula I, as set forth above, wherein S comprises a core enzymatically cleavable amino acid motif, such as, for example, X-Pro-Leu-Gly-Val-Arg-X-X-X, wherein X is any natural or synthetic amino acid, e.g., any of the natural 23 amino acids, stereoisomers thereof, or other synthetic amino acids.

In still a further embodiment, the present invention provides one or more imaging agents of formula I, as set forth above, wherein S is the oligopeptide Gly-Pro-Leu-Gly-Val-Arg-Gly-Lys-Gly-Gly (SEQ ID NO: 10).

In another embodiment, the present invention provides one or more imaging agents of formula I, as set forth above, wherein one or more amino acids have the D configuration. In a preferred embodiment, the present invention provides one or more imaging agents of formula I, as set forth above, wherein S is the oligopeptide Gly-Pro-Leu-Gly-Val-Arg-Gly-D-Lys-Gly-Gly, wherein the amino acid lysine has the D configuration, and wherein the remaining amino acids have the L configuration.

In an embodiment, the present invention provides one or more imaging agents of formula I, as set forth above, wherein Q is chemically, e.g., covalently, linked either directly or indirectly to a separate amino acid of the enzymatically cleavable oligopeptide.

In another embodiment, the present invention provides one or more imaging agents of formula I, as set forth above, wherein Q is a non-fluorescent fluorescence quencher.

In a further embodiment, the present invention provides one or more imaging agents of formula I, as set forth above, wherein Q can include, but is not limited to DABCYL, DABSYL, Eclipse® DarkQuencher, ElleQuencher™ (Eurogentec, S.A., Seraing, Belgium), Iowa Black® Dark Quenchers (Iowa Black FQ, Iowa Black RQ) (Integrated DNA Technologies, Coralville, Iowa), Black Hole Quencher™ Dyes (Black Hole Quencher-1, Black Hole Quencher-2, Black Hole Quencher-3 (BHQ-3) (Biosearch Technologies, Inc., Novato, Calif.)), Blackberry Quencher 650 (Berry and Associates, Inc., Dexter, Mich.), and QSY® Dyes (QSY-7, QSY-9, QSY-21) (Invitrogen, Carlsbad, Calif.).

In yet another embodiment, the present invention provides one or more imaging agents of formula I, as set forth above, wherein Q is BHQ-3.

The structures of the quenchers are depicted in FIGS. 21A-21C. The structures of the quenchers Iowa Black FQ and Iowa Black RQ are proprietary.

In another embodiment, the present invention provides one or more imaging agents of formula I, as set forth above, wherein when administered to a subject in vivo, the agent will exhibit maximum fluorescence in less than 24 hours, 12 hours, or 6 hours.

In a further embodiment, the present invention provides one or more imaging agents of formula I, as set forth above, wherein when administered to a subject in vivo, the agent will exhibit maximum fluorescence in less than 2 hours.

In an embodiment, the present invention provides a composition comprising one or more imaging agents of formula I, as set forth above, and an acceptable carrier.

In accordance with an embodiment of the present invention, the imaging agents of the present invention generally comprise a NIR dye, an oligopeptide as a substrate for a protease of interest, a fluorescence quencher, and PEG or a targeting ligand. The oligopeptide substrate amino acid sequence was synthesized by standard solid-phase Fmoc peptide chemistry. The imaging agents of the present invention were synthesized through serial conjugation of the F, Q and M moieties and deprotection of the substrate peptide in solution, followed by preparative reversed-phase high-performance liquid chromatography (RP-HPLC) purifications. The final synthesized products were confirmed by analytical RP-HPLC and LC-mass spectroscopy.

In an embodiment, the present invention provides a method of identifying a cell or a population of cells in vivo expressing a protease of interest comprising a) contacting the cell or a population of cells expressing a protease of interest with at least one or more imaging agents of formula I, as set forth above, which is selectively cleavable by a protease of interest, b) allowing the imaging agent to be selectively cleaved the protease of interest in the cell or population of cells, and c) detecting the presence of the imaging agent after being cleaved by the protease of interest in the cell or population of cells.

In another embodiment, the cell or population of cells identified in the above method, is a tumor cell.

In a further embodiment, the protease of interest in the above method is associated with the disease of pulmonary fibrosis, liver fibrosis, and/or cancer.

In an embodiment, the present invention provides a method of diagnosing a disease in a subject comprising a) administering to a subject suspected of having said disease, one or more imaging agents of formula I, as set forth above, which is selectively cleavable by a protease of interest, the cleavage of which indicates the presence of the disease, wherein said imaging agent is at least one of the above identified imaging agents, b) allowing the imaging agent to be cleaved by the protease of interest, c) detecting the fluorescence of the fluorophore in the imaging agent binding the protease of interest in the subject; and d) determining whether the subject has a disease overexpressing a protease.

In another embodiment, the protease of interest is associated with a disease of pulmonary fibrosis, liver fibrosis, or cancer. In another embodiment, the protease of interest identified in the method of diagnosing a disease in a subject, is associated with tumor growth and the disease is cancer.

In a further embodiment, the protease of interest identified in the method of diagnosing a disease in a subject, is a matrix metalloproteinase.

In an embodiment, the present invention provides a method of treating a disease in a subject comprising a) administering to a subject suspected of having said disease, one or more imaging agents of formula I, as set forth above, which is selectively cleavable by a protease of interest, the cleavage of which indicates the presence of the disease, wherein said imaging agent is at least one of the above identified imaging agents, b) allowing the imaging agent to be cleaved by the protease of interest, c) detecting the presence of the fluorophore in the imaging agent which is being cleaved the protease of interest in the patient; and d) performing image-guided surgery, image-guided microsurgery, image-guided photo dynamic therapy, or image-guided surgery on the subject.

As defined herein, in one or more embodiments, "contacting" means that the one or more imaging agents of the present invention are introduced into a sample having at least one cell, or population of cells, having a protease of interest, and appropriate enzymes or reagents, in a test tube, flask, tissue culture, chip, array, plate, microplate, capillary, or the like, and incubated at a temperature and time sufficient to permit binding of the at least one imaging agent of the present invention to interact with the protease of interest.

In another embodiment, the term "contacting" means that at least one imaging agent of the present invention is introduced into a subject, preferably a subject receiving treatment for a disease, and the at least one imaging agent is allowed to come in contact with the one disease related cell or population of cells having a protease of interest in vivo.

Accordingly, an embodiment of the present invention provides a method for obtaining a diagnostic image in a subject or patient. In particular, an embodiment of the method comprises administering to the subject or patient, at least one or more imaging agents of the present invention, in an amount effective to provide an image, and exposing the subject or patient to an energy source, whereupon a diagnostic image in the subject or patient is obtained. The diagnostic image can be, for example, obtained using an optical camera or video device, preferably a near-infra red optical imaging camera.

As defined herein, in one or more embodiments, the term "oligopeptide" as used herein includes polypeptides and refers to a single chain of amino acids connected by one or more peptide bonds.

The term "selectively cleavable" in the context of the embodiments of the present invention means placing at least one of the imaging agents of the present invention in proximity to a specific protease of interest, such as in solution, or in vivo, in order for the specific protease of interest to hydrolyze at least one specific peptide bond on the specifically cleavable oligopeptide S.

In accordance with the present invention, the term "Near-IR dye" or "NIR dye" means a dye which fluoresces in the 670-1000 nm range at which biomolecules and polyaromatic hydrocarbons exhibit low background fluorescence due to reduced light scattering.

Embodiments of the invention include a process for preparing compositions comprising the imaging agents of the present invention and a carrier. With respect to compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active imaging agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular imaging agent used in the composition, as well as by the particular method used to administer the composition. Accordingly, there are a variety of suitable formulations of the composition of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the imaging agents of the present invention, administered should be sufficient to effectively target the cell or population of cells in vivo, such that the fluorescence resulting from the binding of the imaging agents to the cells and their subsequent cleavage, provides a fluorescent signal that can be detected, in the subject over a reasonable time frame. The dose will be determined by the efficacy of the particular imaging agent and the location of the target population of cells in the subject, as well as the body weight of the subject to be treated.

The dose of the imaging agent of the present invention also will be determined by the existence, nature and extent of any adverse side effects that might accompany the administration of a particular imaging agent. Typically, an attending physician will decide the dosage of the imaging agent with which to treat each individual subject, taking into consideration a variety of factors, such as age, body weight, general health, diet, sex, compound to be administered, route of administration, and the severity of the condition being treated. By way of example, and not intending to limit the invention, the dose of the imaging agent can be about 0.001 to about 1000 mg/kg body weight of the subject being treated, from about 0.01 to about 10 mg/kg body weight, and from about 0.1 mg to about 1 mg/kg body weight.

The imaging agents of the present invention may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

With respect to the inventive methods, the disease can include cancer. Cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. The term "cancer," as used herein, also includes metastatic cancer.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

As used herein, the term "detection" or "imaging" or means the use of certain properties of fluorescent molecules or dyes and the light emitted from the excited fluorescent dye to diagnose or treat various medical conditions. Without being limited to any particular theory, in an embodiment of the present invention, an imaging agent of the present invention is injected intravenously into the subject which then concentrates in the target cells or organ of interest. By placing a camera that senses the emitted light from the fluorescent dye at the proper emission wavelength over the body, an image of the target cells or organ of interest can be created. The imaging agents of the present invention can be detected by suitable devices such as fluorimeters, spectrophotometric detectors, cameras and the like, preferably a near-infrared intraoperative fluorescence imaging system.

EXAMPLES

The following examples further illustrate the invention but, of course, should not be construed as in any way limiting its scope.

Cell Culture and Animal Models.

Squamous cell carcinoma SCC-7 were cultured in RPMI 1640 medium containing 10% (v/v) fetal bovine serum (Invitrogen, Carlsbad, Calif.) supplemented with penicillin (100 μg/ml) and streptomycin (100 μg/ml) at 37° C. with 5% $CO_2$. The SCC-7 tumor model was developed by subcutaneous injection of $1\times10^6$ cells into the right front flank of female athymic nude mice (Harlan Laboratories, Indianapolis, Ind.). The mice were used for optical studies when the tumor volume reached about 300 mm$^3$. All animal studies were conducted in accordance with the principles and procedures outlined in the NRC Guide for the Care and Use of Laboratory Animals and were approved by the Institutional Animal Care and Use Committee of the Clinical Center, National Institutes of Health.

Synthesis of the Imaging Agents.

The imaging agents of the present invention comprise generally: i) a NIR dye, such as Cy5.5, for example, (ex/em: 675/695 nm); ii) a substrate for a protease of interest, such as the matrix metalloproteinase (MMP) substrate GPL-GVRGKGG (SEQ ID NO: 10) (the recognition site is indicated by italics with the cleavage site between Gly and Val); iii) a fluorescence quencher, such as the Cy5.5 quencher, BHQ-3 (maximum abs. 650 nm), for example, and iv) PEG. The peptide sequence was synthesized by standard solid-phase Fmoc peptide chemistry. The imaging agents of the present invention were synthesized through serial conjugation and deprotection of substrate peptide in solution, followed by preparative reversed-phase high-performance liquid chromatography (RP-HPLC) purifications. The final products were confirmed by analytical RP-HPLC and LC-mass spectroscopy. Cy5.5-NHS was purchased from GE Healthcare (Piscataway, N.J.) and BHQ-3 NHS ester was obtained from Biosearch Technology (Navato, Calif.). Amino PEG analogs $NH_2$—$R_1$ were purchased from Quanta Biodesign (Powell, Ohio) and Sigma-Aldrich (St-Louis, Mo.). All other chemicals were of analytical grade and were purchased from Sigma-Aldrich.

In Vitro Enzyme Test.

The activity of the imaging agents of the present invention was investigated in vitro by incubating the agents (15 nM) in a reaction buffer (50 mM Tris-HCl, 10 mM $CaCl_2 \cdot 2H_2O$, 0.15 M NaCl, 0.05% Brij35 (a nonionic polyoxyethylene surfactant), pH 7.8, TCNB buffer) containing an appropriate amount of activated MMPs. Recombinant human MMPs were activated with 2.5 mM p-aminophenylmercuric acetate (APMA) in the reaction buffer for 1 to 2 hours at 37° C. before use. A homophenylalanine-hydroxamin acid based broad-spectrum MMP inhibitor (referred to herein as MMP-I) (MMP Inhibitor III, Merck KGaA, Darmstadt, Germany) was used for the MMP inhibition test. Fluorescence intensity was monitored using a spectrofluorometer equipped with micro-well plate reader (F-7000 Fluorescence Spectrophotometer, Hitach, Tokyo, Japan) every 10 minutes at 37° C. The excitation wavelength was set at 675 nm and emission spectra were recorded from 680 to 800 nm.

In Vivo Imaging.

Optical image acquisition and analysis were done using a Maestro 2 imaging system (Cambridge Research & Instrumentation, Inc. (CRI), Woburn, Mass.). The imaging agents of the present invention (100 μl in PBS pH 7.4, 300 nM) and MMPSense 680™ (150 μl, as recommended by the manufacturer, VisEn, Bedford, Mass.) were injected via tail vein. Imaging was performed for 24 hours using the Maestro 2 system configured for Cy5.5 detection at the indicated time points after the injection of the probes. For video imaging, 100 μl of the MMP-$P_{12}$ was injected via tail vein catheter and imaging was performed about every 10 seconds for the first 5 minutes, about 15 seconds for 5 to 30 minutes, and about 20 seconds for 30 to 60 minutes, respectively, using Maestro's DyCE function. To inhibit the MMP expression, MMP-I (1 mM) was injected intratumorally 30 minutes before the intravenous injection of the imaging agent. Images were normalized and analyzed by using Maestro software. For quantitative comparison, the regions of interest (ROI) were drawn over tumor (T) and normal tissue (N, muscle), and the average signal ($\times 10^6$ photons$\times$cm$^{-2}\times$s$^{-1}$) for each area was measured. Results were presented as means±s.d. for a group of 3-6 animals.

Ex Vivo Biodistribution.

At 4 hours after injection of the imaging agents, mice were sacrificed and tumors and major organs were carefully excised and rinsed with saline. Excised samples were immediately imaged and analyzed by using the Maestro 2 software. Results were presented as means±s.d. for a group of 3 animals.

Histological Analysis.

Excised tumor tissue slices (4 μm) were fixed with cold acetone for 20 minutes and dried in air for 30 minutes at room temperature. After blocking with 10% BSA for 30 minutes, the sections were incubated with Rabbit anti-MMP-2, anti-MMP-9 and anti-MMP-13 antibodies (10 μg/ml) for 60 minutes at room temperature in the dark, and then visualized with FITC-conjugated donkey anti-rabbit secondary antibody. Finally, the slices were mounted with DAPI-containing mounting medium under an epifluorescence microscope (Olympus, X81). For NIR fluorescence imaging, tumor slices were viewed by fluorescence microscopy equipped with a Cy5.5 filter.

Example 1

This example demonstrates the synthesis of a series of PEGylated imaging agent embodiments.

Figure 1A:
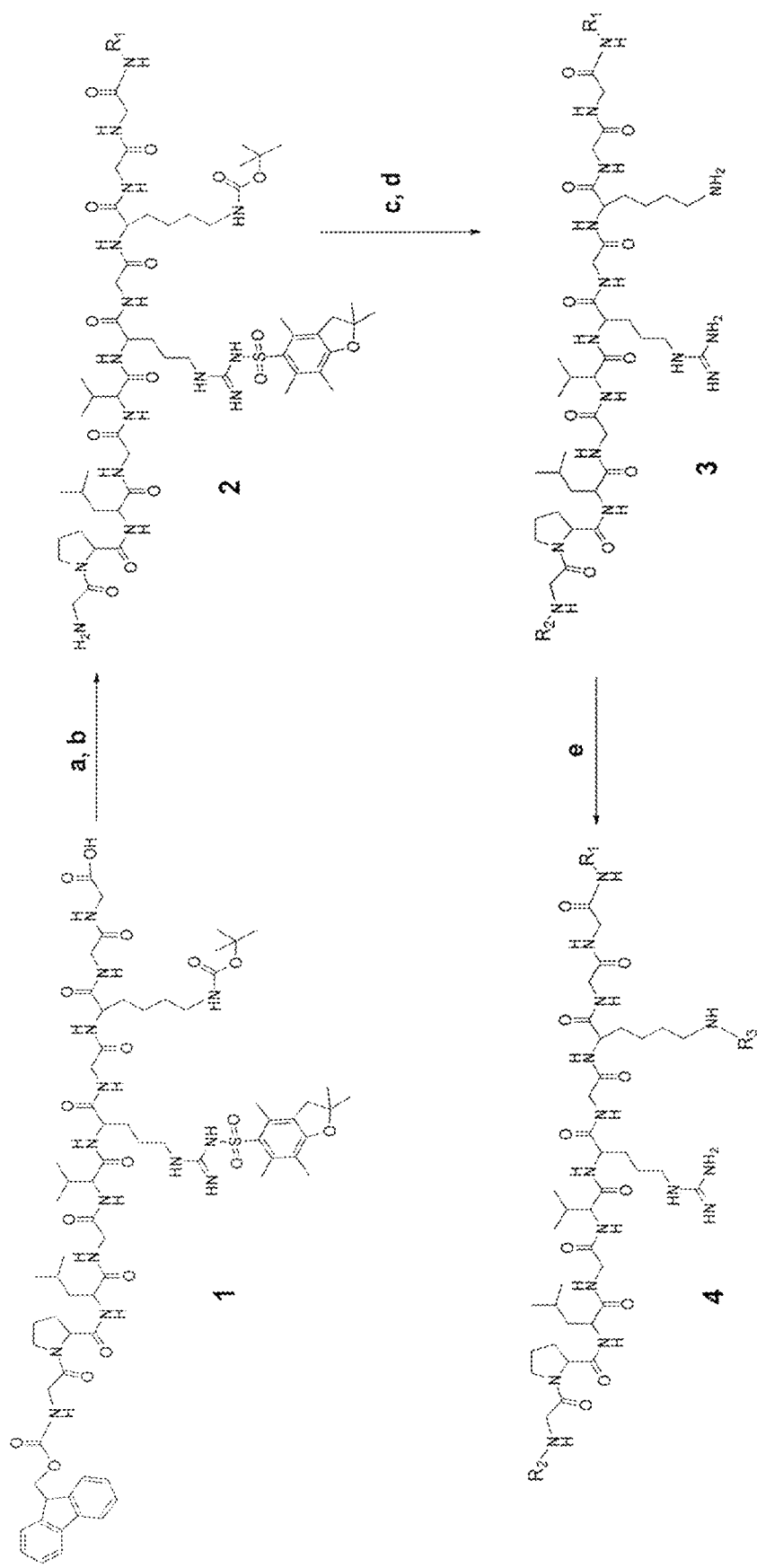
Figure 1B:
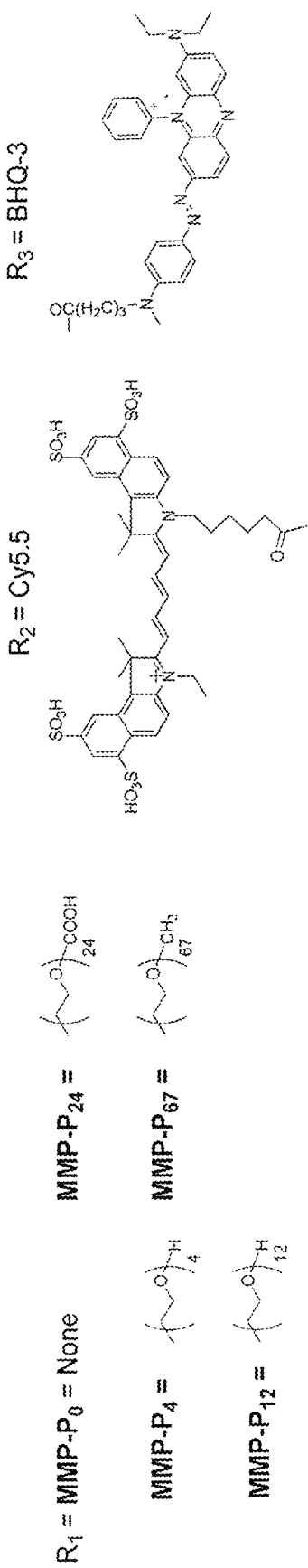
Figure 2A:
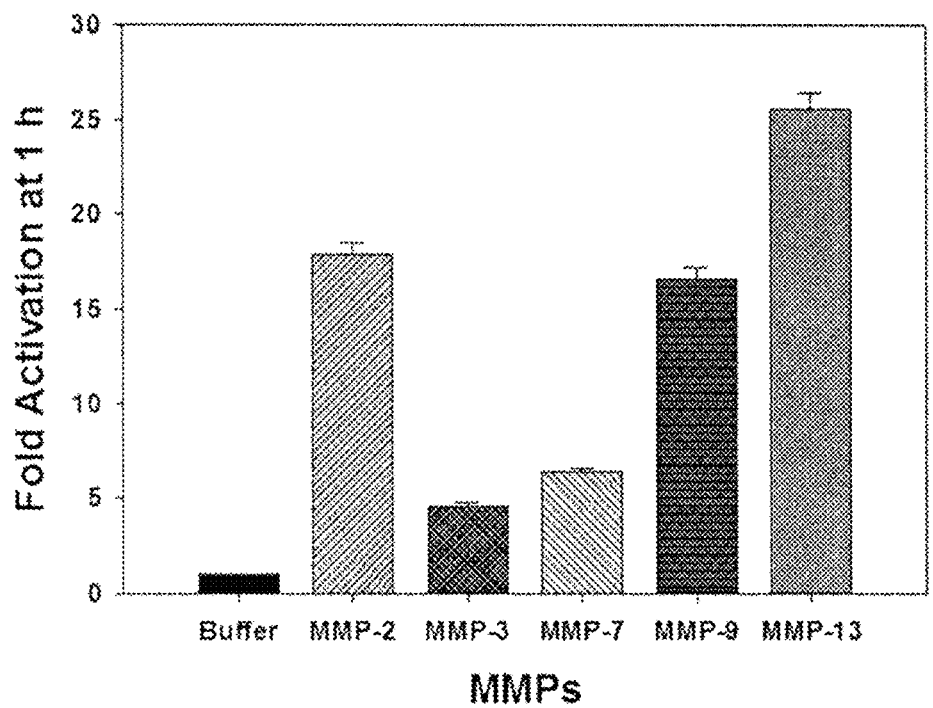
FIG. 2C is a graph depicting fluorescence emission kinetic spectra of the activated MMPs in the presence of MMP-13 with and without a broad-spectrum MMP inhibitor (MMP-I) using the same activation conditions as described for FIG. 2B.
FIG. 2D is a plot of fluorescence intensities of the imaging agents of the present invention (MMP-P$_n$s) in the presence of various concentrations of activated MMP-13 (1, 2, 5, 10, 20, and 40 nM) following a 20-minute incubation. Data are expressed as means±s.d. (n=3).
Figure 2B:
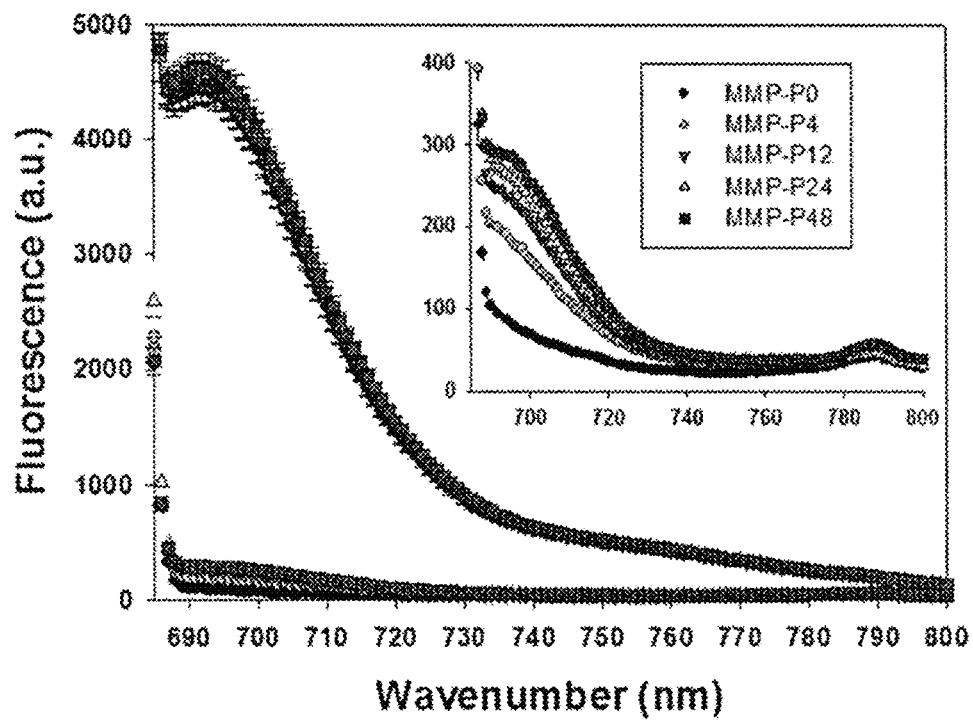
Figure 2C:
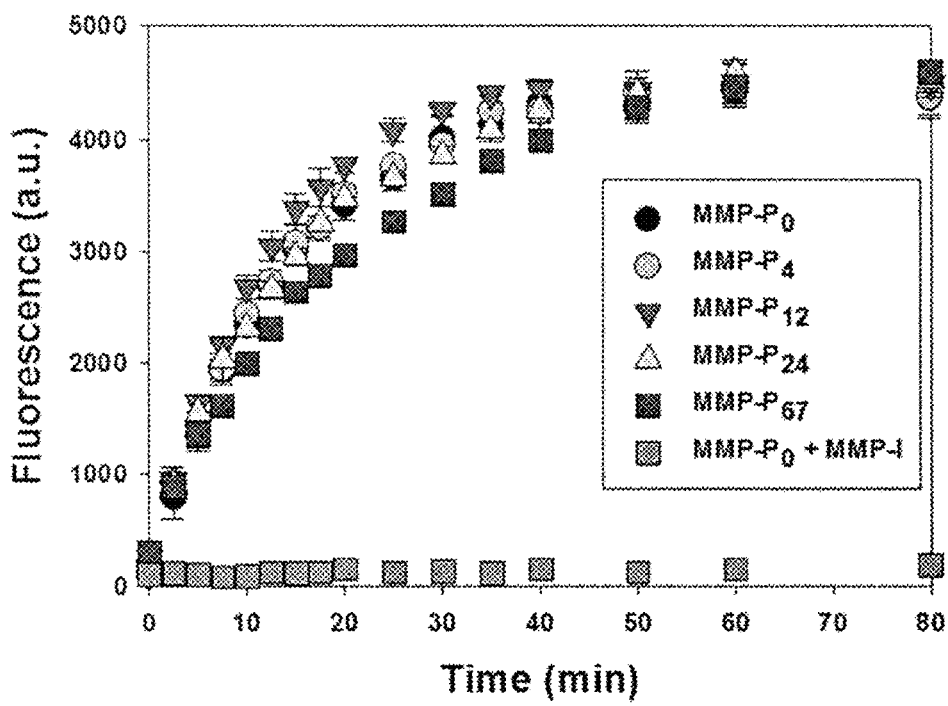
Figure 2D:
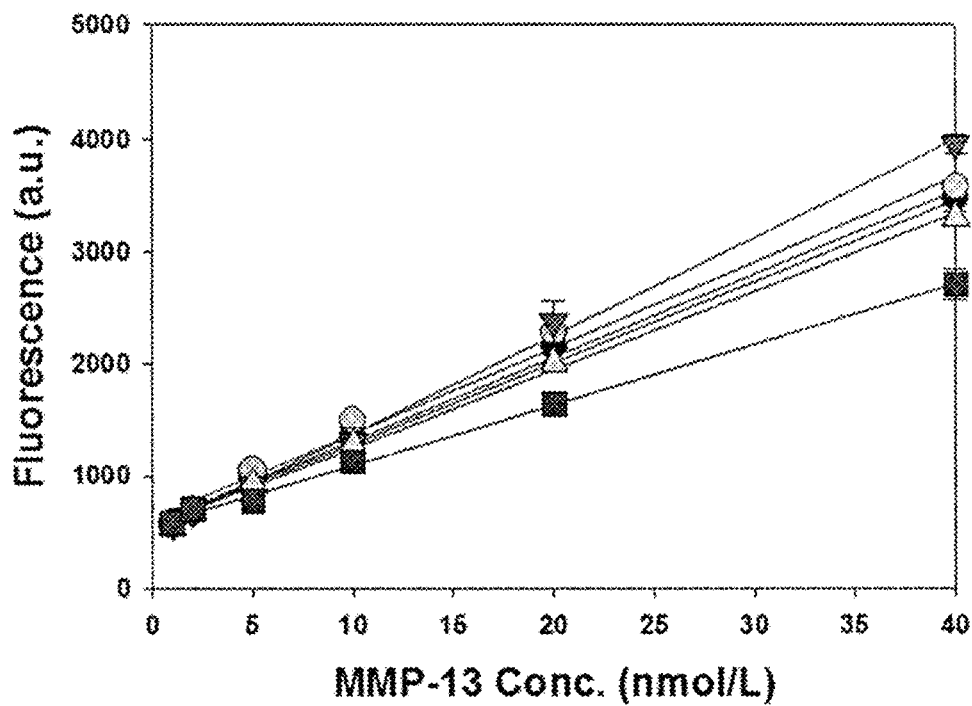

Synthesis of the agents began by preparing MMP activatable imaging agents without PEG, termed MMP-$P_0$. The MMP-$P_0$ consisted of Cy5.5 and BHQ-3 as a near-infrared dye/dark quencher pair, Cy5.5-GPLGVRGK(BHQ-3)GG (SEQ ID NO: 10). Next, PEGs of different sizes were conjugated to the C-termini of the MMP-P$_0$(MMP-P$_n$, where "n" represents the number of repeating ethylene glycol units (—CH$_2$CH$_2$O—) (Table 1 and FIGS. 1A and 1B). MMP-13 was used as a model MMP for in vitro screening since the imaging agent MMP-P$_0$ showed highest specificity against MMP-13 (FIG. 2A). The activity of each MMP-P$_n$ (n=0, 4, 12, 24, and 67) imaging agent was tested by incubating 15 nM of each agent in a 96-well microplate containing the reaction buffer and 40 nM of activated MMP-13, with and without a broad-spectrum hydroxamate-type MMP inhibitor (MMP-I). Fluorescence spectrometry clearly demonstrated that the imaging agents were significantly and fully activated (>25-fold vs. without MMP) in the presence of MMP-13 within an hour (FIG. 2B and FIG. 2C). All MMP-P$_n$ imaging agents showed a linear relationship between the activated fluorescent signals and MMP-13 concentrations and were able to detect nanomolar concentrations of enzyme (FIG. 2D). The rate of activation was slightly enhanced for MMP-P$_{12}$, which may be due to the improved solubility of the probe by PEG, but decreased when higher MW PEG was conjugated because of a steric-hindrance effect. However, no significant differences among the MMP-P$_n$ imaging agents were observed under the tested in vitro conditions.

TABLE 1

Chemical Structures of the MMP-P$_n$ imaging agents. Molecular weight (MW) of the agent MMP-P$_0$ is 2324.95
Cy5.5-GPLGVRGK(BHQ3)GG-R (SEQ ID NO: 10)

| Imaging Agent | R | MW of R |
|---|---|---|
| MMP-P$_0$ | None | 0 |
| MMP-P$_4$ | -NH(CH$_2$CH$_2$O)$_4$H | 192 |
| MMP-P$_{12}$ | -NH(CH$_2$CH$_2$O)$_{12}$H | 545 |
| MMP-P$_{24}$ | -NH(CH$_2$CH$_2$O)$_{24}$H | 1,145 |
| MMP-P$_{67}$ | -NH(CH$_2$CH$_2$O)$_{67}$H | 3,000 |

Example 2

This example demonstrates that MMP-P$_n$ imaging agents of the present invention can improve the visualization of overexpressed MMPs in vivo.

The MMP-P$_n$s and MMPSense 680™ were administered intravenously into separate MMP-positive SCC-7 tumor-bearing mice. In vivo imaging was performed for 24 hours using a small-animal imaging system.

The inventors surprisingly found that modification of MMP-P$_n$ imaging agents with small MW PEG showed significantly reduced activation time (ultrafast-acting and extended-use) in vivo. FIG. 3 shows representative serial images of mice at selected time points. In contrast to the in vitro activity, MMP-P$_4$ and MMP-P$_{12}$ clearly showed early onset of activation in vivo and provided high NIR fluorescence signals in the MMP-positive tumor region for a longer time compared to other MMP-P$_n$s and MMPSense 680™. The activation of fluorescence signals in the tumor region was enhanced when the MW of the PEG moiety was increased up to 500 Da, and gradually decreased with further increases of PEG MW. MMPSense 680™ showed a slightly positive fluorescent signal in the tumor region 24 hours post injection (data not shown), however, the normalized signal was significantly lower than all MMP-P$_n$ imaging agents, except for MMP-P$_{48}$. The ratio of the signal in the regions of interest (ROI) in the tumor compared to the normal region (T/N) of MMP-P$_{12}$ was up to 3-fold higher than any other tested compounds at any time point (FIG. 4A).

The biodistributions of MMP-P$_0$, MMP-P$_{12}$ and MMPSense 680™ were evaluated ex vivo after careful removal of tumors and other organs, after in vivo imaging, at 4 hours post injection. As shown in FIG. 4B, MMP-P$_{12}$ was activated predominantly in the tumors. Tumor sections were also analyzed. Fluorescence microscopy showed strong fluorescence signal consistent with in vivo imaging and anti-MMP antibody staining (for MMP-2, 9, 13), revealing strong expression of MMPs in SCC7 tumors (data not shown). These results indicate that the targeting of specific proteases by the imaging agents of the present invention, can be tested efficiently and optimized by simple small-MW PEG bioconjugation for in vivo applications in disease models.

Example 3

This example demonstrates the ability to create video imaging of MMP activity in vivo using the imaging agents of the present invention.

The MMP-P$_n$s imaging agents used in Example 2, were then used to create a video image of the activity of MMPs in vivo. To inhibit the activity of MMPs in SCC-7 tumor-bearing mice, MMP-I was intratumorally injected 30 minutes before the probe injection. MMP-P$_{12}$ was injected into mice either directly or following MMP-I treatment, using a tail vein catheter during continuous imaging procedures. The animals were imaged every 10 to 20 seconds for 1 hour and video images were generated by using imaging software (DyCE, CRI, Woburn, Mass.). FIG. 5A shows a typical series of video images. The MMP-P$_{12}$ generated strong NIR fluorescence signals as early as 20 to 30 minutes after the probe injection and enabled clear visualization of MMPs in the tumor region thereafter. In contrast, the overall NIR fluorescent signals were significantly decreased when the activity of MMPs was suppressed by the MMP inhibitor. The mean fluorescent intensity of the tumor ROI and the T/N ratios analyzed from normalized snapshot video images clearly confirm that the fluorescent activation of MMP-P$_{12}$ was inhibited significantly in the presence of MMP-I (FIG. 5B and FIG. 6). These results demonstrate the utility of the imaging agents of the present invention for monitoring expression and inhibition of proteases, in vivo, in real-time.

Example 4

The following examples demonstrate that with the imaging agents of the present invention, when M is a targeting ligand, the ligand will efficiently increase the retention time of the imaging agent in the target region and maintain substrate activity, minimizing nonspecific accumulation and enhancing tumor-to-background signal ratio.

To test the imaging agents comprising a targeting ligand, a cyclic Arg-Gly-Asp-Tyr-Asp peptide, c(RGDyK) (SEQ ID NO: 2) was chosen because it is a well-known $\alpha_v\beta_3$ integrin ligand that is overexpressed on the surface of angiogenic endothelial cells that mediates cell adhesion. A number of c(RGDyK)-labeled MMPs specific fluorogenic imaging agents were synthesized, their enzyme and receptor activity was confirmed in vitro, and enhanced imaging of MMPs in both an $\alpha_v\beta_3$ integrin- and MMP-overexpressing tumor-bearing mouse model was demonstrated Cell Culture.

The U87MG human glioblastoma multiforme cell line was obtained from American Type Culture Collection (ATCC, Manassas, Va.). U87MG cells were cultured in DMEM medium containing 10% (v/v) fetal bovine serum (GIBCO, Grand Island, N.Y.) supplemented with penicillin (100 µg/ml), streptomycin (100 µg/ml), non-essential amino acids (100 µM) and sodium pyruvate (1 mM) at 37° C. with 5% $CO_2$.

Animal Models.

Female athymic nude mice were supplied from Harlan at 4 to 5 weeks of age. The U87MG tumor model was generated by subcutaneous injection of $5\times10^6$ cells in Matrigel (BD Biosciences, Sparks, Md.) into the right front flank of female athymic nude mice at a volume of about 80 µl. The mice were then used for optical studies when the tumor volume reached about 300 $mm^3$. All animal studies were conducted in accordance with the principles and procedures outlined in the Guide for the Care and Use of Laboratory Animals and were approved by the Institutional Animal Care and Use Committee of Clinical Center, NIH.

Peptide Probes.

The peptide sequence of the MMP substrate (compound 1) is the same oligopeptide as described above, and was synthesized by standard solid-phase Fmoc peptide chemistry. To synthesize compound 4 (FIG. 7), 5 mg of compound 1 was dissolved in 500 µl N,N-dimethylformamide (DMF) solution containing 2% diisopropylethylamine (DIPEA). 2 mg N,N,N',N'-Bis(tetramethylene)-O—(N-succinimidyl) uronium hexafluorophosphate (HSPyU) was added into the solution to activate the C-terminal carboxylic group and stirred for 30 minutes at room temperature. Next, 2.5 mg of c(RGDyK) was dissolved in 250 µl DMF solution containing 2% DIPEA and mixed with the activated compound 1. The reaction mixture was stirred at room temperature and monitored by analytical HPLC. To remove the Fmoc group, 10% piperidine was added into the solution and stirred for 30 minutes. The crude product was precipitated in cold ether and the pellet was lyophilized and purified by preparative HPLC. The collected fraction of compound 2 was lyophilized and labeled with Cy5.5 NHS ester in DMF solution containing 2% DIPEA. The reaction solution was precipitated against cold ether, lyophilized, and subjected to $TFA/H_2O/TIS/EDT$ (85/5/5/5, v/v/v/v) cocktail to remove the protection groups. Crude product was purified by preparative HPLC. The desired fraction containing compound 3 was collected and lyophilized. In the last step, BHQ-3 NHS ester was conjugated and the final compound 4 was purified by HPLC on a C-18 semi-preparative column using a linear gradient of 10% to 55% acetonitrile/water (0.1% trifluoroacetic acid), for 30 minutes at a 10 ml/minute flow rate. Compounds 5 and 6 were synthesized by serial conjugations and deprotections of the peptides as described previously, followed by preparative HPLC purification. Compound 7 was synthesized by conjugation of CW800 NHS ester and c(RGDyK) in DMF solution containing 2% DIPEA. The reaction solution was precipitated against cold ether, lyophilized, and purified by HPLC. All purified products were confirmed by analytical HPLC and LC/MS, MS calculated/found; 2926.20/2926.18 (data not shown).

In Vitro Enzyme Test.

The fluorogenic properties of the imaging agents of the present invention were examined by incubating the agents in the reaction buffer (100 mM Tris, 200 mM NaCl, 5 mM $CaCl_2$, 0.1% Brij35, pH 7.5) containing 40 nM of APMA-activated recombinant human MMP-2. Fluorescence intensity was monitored using a spectrofluorometer (F-7000 Fluorescence Spectrophotometer, Hitach, Tokyo, Japan) every 10 minutes at 37° C. using a quartzose cuvette. The excitation wavelength was set at 675 nm and emission spectra recorded from 680 to 800 nm. The same experimental conditions were applied to various concentrations of MMP-2 in the presence of fixed concentrations of the imaging agents.

Receptor Binding Assay.

Briefly, the U87MG cell line was cultured in DMEM medium containing 10% (v/v) fetal bovine serum supplemented with penicillin (100 µg/ml), streptomycin (100 µg/ml), non-essential amino acids (100 mM) and sodium pyruvate (1 mM) at 37° C. with 5% $CO_2$. After reaching 80% confluence, cells were scraped off and suspended with binding buffer (25 mM 2-amino-2-(hydroxymethyl)-1,3-propanediol, hydrochloride (Tris-HCl), pH 7.4, 150 mM NaCl, 1 mM $CaCl_2$, 0.5 mM $MgCl_2$ and 1 mM $MnCl_2$, 0.1% bovine serum albumin (BSA)) at a final concentration of $4\times10^6$ cells/ml. In a 96-well plate, $2\times10^5$ U87MG cells/well were incubated with $^{125}$I-Echistatin (0.02 mCi/well, PerkinElmer Inc.) in binding buffer in the presence of different concentrations of c(RGDyK), and the peptide probes at room temperature for 2 hours. After incubation, the plate was washed three times with PBS containing 0.1% BSA, and the radioactivity was measured by y-counting. The $IC_{50}$ values were calculated by nonlinear regression analysis.

In Vivo Optical Imaging.

Optical imaging acquirement and analysis were done using a Maestro 2.10 in vivo imaging system (CRI). U87MG tumor-bearing mice were injected via tail vein with compounds 4, 5, 6, 7, and 4 with MMP inhibitor or unlabeled c(RGDyK), respectively, under isoflurane anaesthesia (n=3 per group). The molar concentration of each samples were calculated by the sample weight. At 1, 2, 3, and 4 hours post-injection, the mice were subjected to optical imaging using appropriate filters for Cy5.5 and CW800. For the inhibition experiment, MMP inhibitor was intratumorally injected into tumor bearing mice 30 minutes before the imaging agent injection. After image acquisition, spectral unmixing yielded the pseudocolor images of the pure spectrum of respective dyes. Images were normalized and analyzed using Maestro software. For quantitative comparison, regions of interest (ROI) were drawn over tumors and muscle, and the average signal (106 photons×$cm^{-2}$×$s^{-1}$) for each area was measured. Values were expressed as mean±s.d. for a group of three animals.

Ex Vivo Biodistribution.

Ex vivo imaging of excised tumor and organs further confirmed the targeting specificity and activation of the probes (data not shown). At 4 hours post-injection, the mice were sacrificed and major organ tissues and tumors were harvested, and placed on black paper for ex vivo imaging. For quantitative comparison, ROIs were drawn over tumors and the other organs, and the average signal for each area was measured. The results were presented as the average scaled signal from the organs and tumors. Values were expressed as mean±s.d. for a group of three animals.

Immunohistochemistry.

Frozen U87MG tumor tissue slices (4 µm) from the tumor bearing nude mice were fixed with cold acetone for 20 minutes and dried in air for 30 minutes at room temperature. After blocking with 10% BSA for 30 minutes, the sections were incubated with Rabbit anti-integrin $\alpha_v\beta3$ and Rabbit anti-MMP-2 and antibodies (10 µg/ml) for 60 minutes at room temperature in the dark. Samples were then visualized with FITC-conjugated donkey anti-rabbit secondary antibody. Finally, the slices were mounted with DAPI-containing mounting medium under an epifluorescence microscope (Olympus, X81). The tumor slices were also observed directly after mounting with DAPI-containing mounting medium under an epifluorescence microscope and fluorescence images were taken using Cy5.5 filter settings.

Statistical Analysis.

Results were expressed as mean±s.d. Two-tailed paired and unpaired Student's t tests were used to test differences within groups and between groups, respectively. P values <0.05 were considered statistically significant.

Example 5

This example demonstrates the ability of the imaging agents of the present invention having a ligand, bind the target protease with specificity.

MMP specificity of the imaging agent compound 4 was compared to that of compound 6 to confirm whether conjugation of the targeting ligand affects its enzyme specificity. In vitro enzyme specificity was measured in the reaction buffer (100 mM Tris, 200 mM NaCl, 5 mM $CaCl_2$, 0.1% Brij35, pH 7.5) containing activated MMP-2 with, and without a homophenylalanine-hydroxamine acid based broad-spectrum MMP inhibitor (EMD Bioscience) using a spectrofluorometer. The MMP-2 was activated by incubation of 2.5 mM of p-aminophenyl mercuric acid (APMA) in the reaction buffer for 2 hours at 37° C. prior to use. As shown in FIG. 9A, MMP-2 (40 nM) treatment of 4 and 6 (15 nM) resulted in an increased recovery of the NIR fluorescence signal and showed greater than 20-fold increase relative to the control sample without MMP-2. The fluorescence recovery of compound 4 was inhibited in the presence of the MMP inhibitor indicating imaging agent selectivity. Similar experiments were performed by incubating compound 4 in the presence of different concentrations of MMP-2 (0, 2, 5, 10, 20, 40 nM) and the recovery of fluorescence was dependent on the MMP-2 concentration (FIG. 9B). The overall MMP specificity of compound 4 against MMP-2 was similar to that of compound 6. These results indicate that conjugation of the targeting ligand c(RGDyK) did not alter the MMP specificity of the imaging agent.

Example 6

This example demonstrates the effect of a fluorogenic peptide on the $\alpha_v\beta_3$ binding affinity of c(RGDyK) in the imaging agents of the present invention.

The effect of a fluorogenic peptide on the $\alpha_v\beta_3$ binding affinity of c(RGDyK) was measured by a competitive cell-binding assay in U87MG cells. $^{125}$I-eschistatin was used as a specific radioligand for competitive displacement. The U87MG cell is known to have high $\alpha_v\beta_3$ integrin density on the cell surface. All analogs containing c(RGDyK) ligand maintained reasonable binding affinities to its receptor. The $IC_{50}$ values of c(RGDyK), and compounds 4, 5, and 7 were 592, 267, 184, and 456 nM, respectively (FIG. 10). Next, receptor specificity of the probes in cell culture was verified by fluorescent microscopic studies. The probes were incubated in fixed U87MG cells with and without a blocking dose of c(RGDyK) (10 μM). Since compound 5, the non-quenched form of compound 4, showed similar $\alpha_v\beta_3$ binding to compound 4, compound 5 was used for in vitro cellular imaging studies. Strong positive fluorescent signals on the cell membranes were observed after 30 minutes of incubation at 37° C. (data not shown). Since receptor blocking with an excess c(RGDyK) significantly decreased binding of compound 5, the probe exhibits significant receptor specificity. Taken together, an NIR fluorogenic probe containing c-(RGDyK) ligand showed specific activities against both MMP-2 and $\alpha_v\beta_3$ highlighting that compound 4 is useful as an $\alpha_v\beta_3$ receptor-targeted MMP-specific imaging agent.

Example 7

This example illustrates how the receptor-targeting ligand on the imaging agents of the present invention can enhance the visualization of extracellular protease expression in vivo.

About 3 nmol of compound 4 was intravenously injected into U87MG tumor-bearing mice treated with, and without an MMP inhibitor. In order to inhibit the activity of MMPs in U87MG tumor, MMP inhibitor was intratumorally injected 30 minutes before the injection of compound 4. To demonstrate the superiority of the receptor targeted fluorogenic imaging agent of the present invention over existing NIR dye-labeled receptor-targeted peptides in tumor imaging, compounds 5 and 7 (0.5 nmol) were each also injected into an U87MG tumor model. It should be noted that only a limited dose of dye-labeled peptide probe like compounds 5 and 7 can be injected for whole body imaging, because of its high fluorescent background from the dye. In contrast, since fluorogenic probes are strongly quenched and a majority of the probe is activated at the target site, higher doses of the imaging agents of the present invention can be injected to enhance the ratio of region-of-interest (ROI) signal of tumor to normal tissue, muscle (T/N), at very early times. After injection, in vivo optical imaging was performed for 4 hours using a small animal imaging system (Maestro 2) equipped with appropriate filters for Cy5.5 and CW800. FIG. 11 shows representative serial images of mice at selected time points. Both compounds 4 and 6 enabled visualization of MMP expression in an MMP positive tumor, but compound 4 provided brighter NIR fluorescent images compared to compound 6 from 1 hour post-injection. As expected, when MMP expression was inhibited by MMP inhibitors, the NIR fluorescence signal from the tumor was significantly reduced. In addition, tumor uptake was effectively blocked at 30 minutes post-injection with an excess amount of unlabeled c(RGDyK) (200 nmol) with compound 4 demonstrating the c(RGDyK)-mediated specific binding of compound 4 in vivo (data not shown).

Like other conventional types of NIR dye-labeled peptide probes, compounds 5 and 7 showed gradually increased fluorescent signals in the tumor after the probe was slowly cleared from the blood and other organs. T/N ratios are illustrated in FIG. 12A. Compound 4 showed enhanced T/N and were up to 2.3, 1.5, 2.0, and 3.4-fold higher than compounds 5, 6, 7, and 4 treated with an inhibitor, respectively. After whole-mouse imaging at a 4 hour time point, tumors and organs were carefully removed and the biodistribution of compounds 4 and 6 was evaluated (FIG. 12B). Ex vivo biodistribution studies also indicated that compound 4 was predominantly activated in the tumors among other organs and compared to other groups. Selective tumor tissues were also analyzed by immunohistochemistry and NIR fluorescent microscopy to confirm the expression of biomarkers and accumulation of the probe (data not shown). $\alpha_v\beta_3$ integrin and MMP-2 antibody staining revealed strong expression of biomarkers in U87MG tumors and NIR fluorescence microscopy images showed a strong Cy5.5 signal, consistent with in vivo imaging (data not shown).

Example 8

This example demonstrates the use of the imaging agents of the present invention in a model of pulmonary fibrosis (PF).

PF is a progressive fibrosing lung condition pathologically characterized by various degrees of inflammation and fibrosis of the lung parenchyma. Since the etiopathogenesis of PF is complicated and not fully understood, the management of PF remains a challenge. Positron emission tomography (PET) and high resolution computed tomography (HRCT) are used in PF diagnosis in the clinic with limited sensitivity and specificity. Both MMP-2 and MMP-9 are known to be expressed in subepithelial myofibroblasts and occasionally in areas of denuded alveolar basement membranes. The increased activity of such MMPs leads to the breakdown of the interstitial matrix and triggers certain growth factors, which play an important mechanistic role in PF pathogenesis. Herein the inventors monitored the progression of PF in a PF animal model by imaging MMP expression in vivo using the agents of the present invention (MMP-$P_{12}$). MMP expression in a bleomycin-induced mouse PF model (BLM) at different disease stages (3, 7, 14 and 21 days) was quantified by RT-PCR, Western blot and immunostaining. As seen in FIGS. 13A-C, MMP-2 is highly expressed in PF model and expression level was dependent on the developmental stage of lung fibrosis. MMP-activated fluorescence images were acquired at different time points after bleomycin induction. FIG. 14A shows representative in vivo images of whole-body animals at selected time points. The ratio of the signal in the region of interest (ROI) of the lung revealed that fluorescent signals gradually increased up to 21 days after the bleomycin treatment (FIG. 14B) and was correlated with MMP-2 expressions verified by ex vivo assays. After scanning, mice were sacrificed, and major organs were subjected to ex vivo imaging and biodistribution studies for fluorescence signal quantification. As shown in FIGS. 15A and 15B, a good correlation was found between the stage of pulmonary fibrosis and fluorescence intensity that reflects MMP expression, indicating that the probe is a promising tool for PF imaging.

Animal Model:

Bleomycin-induced pulmonary fibrosis mouse model (BLM) was used. In brief, C57BL6/J mice were anesthetized with ketamine-xylazine, then were administered with bleomycin (1.2 U/kg per mouse, n=9) or saline (n=3) as control by intratracheal intubation (both given in 50 µl sterile saline). Bleomycin solution was prepared immediately before administration. At day 3, 7, 14 and 21 after bleomycin treatment, mice were fasted for 6 hours and subjected to optical imaging followed by intravenous injection of the agent. In vivo imaging was performed at 2 hours after injection and images were analyzed using the Maestro 2.10 in vivo imaging system.

Ex Vivo Characterizations:

The expression of MMP-2 in lung from a PF model at different stages (at day 3, 7, 14 and 21) was characterized by hematoxylin and eosin (H&E) staining, RT-PCR and western blot analysis with MMP-2 antibody. For ex vivo biodistribution study, mice were sacrificed after the whole-body imaging and major organs were carefully harvested and imaged using Maestro. For quantitative comparison, ROI was calculated.

Example 9

This example demonstrates the use of imaging agents of the present invention for use in non-invasive monitoring of liver fibrosis.

Chronic liver disease is an important cause of morbidity and mortality. The gold standard for diagnosis and assessment of liver disease such as fibrosis and cirrhosis is currently based on liver biopsy. Liver fibrosis (LF) is the result of chronic recurrent injury to the hepatic parenchyma. LF is the final common pathway for most chronic liver disease and can ultimately leads to liver cirrhosis, liver failure and liver cancer. Although liver biopsy remains the gold standard diagnostic tool, a noninvasive imaging method of detecting LF will help improve early diagnosis of liver diseases and patient compliance in the clinic. Since MMPs are also known to be important players and overexpressed in fibrosis because of their collagen-cleaving activity, the agent can be used as an imaging agent for liver fibrosis diagnosis. In addition, the agent can also be used as a tool for screening MMP inhibitors that can potentially decrease liver fibrogenesis. In the present example, the progression of LF in a carbon tetrachloride ($CCl_4$)-induced LF animal model was monitored by imaging MMP expression using the agents of the present invention (MMP-$P_{12}$). FIG. 16A demonstrates representative ex vivo images of the dissected liver following intravenous administration of the agent at selected time points after $CCl_4$ induction (0, 2, 4, and 8 weeks). ROI analysis of the liver demonstrated that fluorescent signals started to increase compared to control group after 4 weeks of $CCl_4$ treatment. The high fluorescent signals in the liver were maintained up to 8 weeks (FIG. 16B).

Animal Models and Ex Vivo Imaging:

Strain A/J male mice were randomly assigned to two groups, a control group (n=3) and a $CCl_4$-treated group (n=9). Mice were treated three times per week for 8 weeks with 50 µl of 40% of $CCl_4$ in olive oil or with vehicle by oral gavage. At the first day of 2, 4 and 8 weeks after $CCl_4$ treatment, mice were fasted for 6 hours and the agent was intravenously injected. Mice were sacrificed at 4 hours after injection of the agent and the liver was carefully harvested and imaged using the Maestro system. For quantitative comparison, ROI was calculated.

Example 10

This example demonstrates the differential uptake in SCC7 tumors, organs, and tissues of L-MMP-P12 and D-MMP-P12. The structures of L-MMP-P12 and D-MMP-P12 are depicted in FIGS. 17A and 17B and differ in that D-MMP-P12 has a D-lysine in place of the L-lysine present in L-MMP-P12.

In Vivo Optical Imaging.

Optical imaging acquirement and analysis were done using a Maestro 2.10 in vivo imaging system (CRI). SCC7 tumor-bearing mice were injected via tail vein with L-MMP-P12 or D-MMP-P12 under isoflurane anaesthesia (n=3 per group). The molar concentration of each samples was calculated by the sample weight. At 15, 30, 60, and 120 min post-injection, the mice were subjected to optical imaging using appropriate filters for Cy5.5 and CW800. After image acquisition, spectral unmixing yielded the pseudocolor images of the pure spectrum of respective dyes. Images were normalized and analyzed using Maestro software. For quantitative comparison, regions of interest (ROI) were drawn over tumors and muscle, and the average signal (106 photons×$cm^{-2}$×$s^{-1}$) for each area was measured. Values were expressed as mean±s.d. for a group of three animals.

Representative in vivo NIR fluorescence images of MMP- and $α_v β3$ integrin receptor-positive SCC7 tumor-bearing mice are depicted in FIG. 18A. The mouse on the left in each image was treated with L-MMP-P12 while the mouse on the right was treated with D-MMP-P12.

The region of interest analysis of SCC7 tumors at indicated time points postinjection of L-MMP-P12 or D-MMP-P12 is depicted in FIG. 18B.

Ex Vivo Biodistribution.

Ex vivo imaging of excised tumor and organs further confirmed the targeting specificity and activation of the probes. At 30 min and 120 min post-injection, the mice were sacrificed and major organ tissues and tumors were harvested, and placed on black paper for ex vivo imaging. For quantitative comparison, ROIs were drawn over tumors and the other organs, and the average signal for each area was measured. The results were presented as the average scaled signal from the organs and tumors. Values were expressed as mean±s.d. for a group of three animals.

The results are shown in FIGS. 19A and 19B. FIGS. 19A and 19B are bar graphs depicting the ratio of tumor signals versus other major organs of D-MMP-P12 and L-MMP-P12 in SCC7 tumor-bearing mice at 30 min (FIG. 19A) and 120 min (FIG. 19B). Data are expressed as mean±s.d. (n=3). * P<0.05. T=tumor; Lu=lung; Kd=kidney; Mu=muscle, Li=liver.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An imaging agent of formula I:

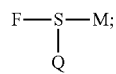

(I)

wherein:
F is a near infrared fluorophore selected from the group consisting of fluorescein isothiocyanate (FITC, green), cyanine dyes Cy2, Cy3, Cy3.5, Cy5, Cy5.5, Cy7, Cy7.5, Texas Red, and IRDye800CW;
S is an oligopeptide consisting only of Gly-Pro-Leu-Gly-Val-Arg-Gly-Lys (SEQ ID NO: 3), wherein the oligopeptide does not contain any additional amino acids;
Q is a fluorescence quencher molecule selected from the group consisting of DABCYL, DABSYL, Black Hole Quencher-1 (BHQ-1), Black Hole Quencher-2 (BHQ-2), Black Hole Quencher-3 (BHQ-3), Blackberry Quencher 650, QSY-7, QSY-9, and QSY-21; and
M is polyethylene glycol having a molecular weight of 104 Daltons to 588 Daltons,
and wherein F, Q and M are linked to separate amino acids of the oligopeptide.

2. The imaging agent of claim 1, wherein the near infrared fluorophore is selected from the group consisting of Cy5.5, Cy7, Cy7.5, and IRDye800CW.

3. The imaging agent of claim 1, wherein Q is Black Hole Quencher-3 (BHQ-3) or QSY-7.

4. A composition comprising the imaging agent of claim 1, and a carrier.

5. An imaging agent of formula I:

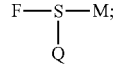

(I)

wherein:
F is a near infrared fluorophore selected from the group consisting of fluorescein isothiocyanate (FITC, green), cyanine dyes Cy2, Cy3, Cy3.5, Cy5, Cy5.5, Cy7, Cy7.5, Texas Red, and IRDye800CW;
S is an oligopeptide consisting only of Leu-Pro-Lys-Gly-Leu (SEQ ID NO: 7), wherein the oligopeptide does not contain any additional amino acids;
Q is a fluorescence quencher molecule selected from the group consisting of DABCYL, DABSYL, Black Hole Quencher-1 (BHQ-1), Black Hole Quencher-2 (BHQ-2), Black Hole Quencher-3 (BHQ-3), Blackberry Quencher 650, QSY-7, QSY-9, and QSY-21; and
M is polyethylene glycol having a molecular weight of 104 Daltons to 588 Daltons,
and wherein F, Q and M are linked to separate amino acids of the oligopeptide.

6. The imaging agent of claim 5, wherein the near infrared fluorophore is selected from the group consisting of Cy5.5, Cy7, Cy7.5, and IRDye800CW.

7. The imaging agent of claim 5, wherein Q is Black Hole Quencher-3 (BHQ-3) or QSY-7.

8. A composition comprising the imaging agent of claim 5 and a carrier.

9. An imaging agent of formula I:

(I)

wherein:
F is a near infrared fluorophore selected from the group consisting of fluorescein isothiocyanate (FITC, green), cyanine dyes Cy2, Cy3, Cy3.5, Cy5, Cy5.5, Cy7, Cy7.5, Texas Red, and IRDye800CW;
S is an oligopeptide consisting only of Arg-Pro-Lys-Pro-Val-Glu (SEQ ID NO: 8), wherein the oligopeptide does not contain any additional amino acids;
Q is a fluorescence quencher molecule selected from the group consisting of DABCYL, DABSYL, Black Hole Quencher-1 (BHQ-1), Black Hole Quencher-2 (BHQ-2), Black Hole Quencher-3 (BHQ-3), Blackberry Quencher 650, QSY-7, QSY-9, and QSY-21; and
M is polyethylene glycol having a molecular weight of 104 Daltons to 588 Daltons,
and wherein F, Q and M are linked to separate amino acids of the oligopeptide.

10. The imaging agent of claim 9, wherein the near infrared fluorophore is selected from the group consisting of Cy5.5, Cy7, Cy7.5, and IRDye800CW.

11. The imaging agent of claim 9, wherein Q is Black Hole Quencher-3 (BHQ-3) or QSY-7.

12. A composition comprising the imaging agent of claim 9, and a carrier.

* * * * *